US007786290B2

(12) United States Patent
Woppmann et al.

(10) Patent No.: US 7,786,290 B2
(45) Date of Patent: Aug. 31, 2010

(54) DOUBLE-STRANDED RIBONUCLEIC ACID WITH INCREASED EFFECTIVENESS IN AN ORGANISM

(75) Inventors: Claudia Woppmann, Gesees (DE); Hans-Peter Vornlocher, Bayreuth (DE); Philipp Hadwiger, Altenkunstadt (DE); Matthias John, Hallstadt (DE); Stefan Limmer, Kulmbach (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 796 days.

(21) Appl. No.: 10/560,336

(22) PCT Filed: Jun. 14, 2004

(86) PCT No.: PCT/US2004/018848

§ 371 (c)(1),
(2), (4) Date: Apr. 26, 2007

(87) PCT Pub. No.: WO2005/014782

PCT Pub. Date: Feb. 17, 2005

(65) Prior Publication Data

US 2007/0275465 A1    Nov. 29, 2007

Related U.S. Application Data

(60) Provisional application No. 60/479,354, filed on Jun. 18, 2003.

(30) Foreign Application Priority Data

Jun. 13, 2003  (EP) .................................. 03013296
Feb. 3, 2004   (EP) .................................. 04002374

(51) Int. Cl.
 *C12Q 1/68* (2006.01)
 *C12P 19/34* (2006.01)
 *C12N 15/63* (2006.01)
 *C07H 21/02* (2006.01)
 *C07H 21/04* (2006.01)

(52) U.S. Cl. .................. 536/24.5; 435/6; 435/91.1; 435/91.31; 435/455; 435/536; 435/23.1

(58) Field of Classification Search .................. 435/6, 435/91.1, 91.31; 514/44; 536/23.1, 24.5
See application file for complete search history.

(56) References Cited

U.S. PATENT DOCUMENTS 7,345,027 B2 * 3/2008 Tolentino et al. ............. 514/44

FOREIGN PATENT DOCUMENTS

| WO | WO 01/60998 | | 8/2001 |
|---|---|---|---|
| WO | WO 02/44321 | * | 6/2002 |
| WO | WO 02/055692 | | 7/2002 |
| WO | WO 02/055693 | | 7/2002 |
| WO | WO 03/012052 | | 2/2003 |
| WO | WO 03/035868 | | 5/2003 |
| WO | WO 03/035869 | | 5/2003 |
| WO | WO 03/062423 | | 7/2003 |
| WO | WO 03/099298 | | 12/2003 |
| WO | WO 2004/011647 | | 2/2004 |

OTHER PUBLICATIONS

Tari, A.M. et al., "Human Bcl-2 Protein DNA #1," Database Geneseq, (2001) Abstract.
Freier, S.M. et al., "Improved free-energy parameters for predictions of RNA duplex stability," Proc. Natl. Acad. Sci. 83:9373-9377 (1986).
Supplementary Partial European Search Report for EP 04 77 6539 dated Mar. 13, 2008.
Elbashir et al. "RNA interference is mediated by 21 and 22-nucleotide RNAs" *Genes and Development* 2001, 15, 188-200.
Elbashir et al. "Functional anatomy of siRNA for mediating efficient RNAi in *Drosophila melanogaster* embryo lysate" *The Embo Journal* 2001, 20(23), 6877-6888.
Futami et al. "Induction of apoptosis in HeLa cells with siRNA expression vector targeted against bcl-2" *Nucleic Acid Research Supplement* 2002, 2, 251-252.
Ocker et al. "Variants of bcl-2 specific siRNA for silencing antiapoptotic bcl-2 in pancreatic cancer" *Gut* 2005, 54, 1298-1308.
Tsujmoto et al. "Human B-cell leukemia/lymphoma 2 (bcl-2) proto-oncogene mRNA encoding bcl-2-alpha protein, complete cds." Database accession No. M13994, Oct. 31, 1994.
Tsujimoto et al. "Analysis of the structure, transcripts, and protein products of bcl-2, the gene involved in human follicular lymphoma" *Proc. Natl. Acad. Sci. U.S.A.* 1986, 83 (14), 5214-5218.

* cited by examiner

*Primary Examiner*—Jane Zara
(74) *Attorney, Agent, or Firm*—Nixon Peabody LLP; Jeffrey N. Townes

(57) ABSTRACT

The present invention relates to a method for the targeted selection of a double-stranded ribonucleic acid (dsRNA) consisting of two single strands that exhibits increased effectiveness in inhibiting the expression of a target gene by means of RNA interference, wherein at least end of the dsRNA comprises a nucleotide overhang of 1 to 4 unpaired nucleotides in length; wherein the unpaired nucleotide adjacent to the terminal nucleotide pair comprises a purine base; and wherein the terminal nucleotide pair on both ends of the dsRNA is a G-C pair, or at least two of the last four consecutive terminal nucleotide pairs are G-C pairs.

31 Claims, 3 Drawing Sheets

DOUBLE-STRANDED RIBONUCLEIC ACID WITH INCREASED EFFECTIVENESS IN AN ORGANISM

RELATED APPLICATIONS

This application claims the benefit of priority to Patent Cooperation Treaty Application number PCT/US2004/018848, filed Jun. 14, 2004; which claims the benefit of priority to European Patent Application serial number 03013296.3, filed Jun. 13, 2003; U.S. Provisional Patent Application Ser. No. 60/479,354, filed Jun. 18, 2003; and European Patent Application serial number 04002374.9, filed Feb. 3, 2004. The entirety of each of them is hereby incorporated by reference.

BACKGROUND OF THE INVENTION

Many diseases (e.g., cancers, hematopoietic disorders, endocrine disorders, and immune disorders) arise from the abnormal expression or activity of a particular gene or group of genes. Similarly, disease can result through expression of a mutant form of protein, as well as from expression of viral genes that have been integrated into the genome of their host. There are numerous therapeutic benefits of the ability to silence selectively these abnormal or foreign genes.

Several therapeutic agents capable of inhibiting the expression of a target gene have been developed, most notably antisense nucleic acid (see, e.g., Skorski, T. et al., Proc. Natl. Acad. Sci. USA (1994) 91:4504-4508). However, antisense approaches, which use either single-stranded RNA or DNA, act in a 1:1 stoichiometric relationship and thus have low efficacy (Skorski et al., supra). For example, Jansen et al. report that relatively high doses (1.7 mg/kg body weight per day, resulting in long term plasma concentrations above 1 mg/L) of antisense RNA specific for the gene bcl2 were required to attain the intended effect of the antisense compound (i.e., 40% reduction in bcl2 expression) (Jansen, B., et al., The Lancet (2000) 356:1728-1733).

Relatively recently, double-stranded RNA molecules (dsRNA) have been shown to block gene expression by virtue of a highly conserved regulatory mechanism known as RNA interference (RNAi). Briefly, the RNA III Dicer enzyme processes dsRNA into small interfering RNA (siRNA) of approximately 22 nucleotides. One strand of the siRNA (the "complementary strand") then serves as a guide sequence to induce cleavage of messenger RNAs (mRNAs) comprising a nucleotide sequence which is at least partially complementary to the sequence of the complementary strand by an RNA-induced silencing complex (RISC) (Hammond, S. M., et al., Nature (2000) 404:293-296). The complementary strand is not cleaved or otherwise degraded in this process, and RISC comprising the complementary strand c an subsequently effect the cleavage of further mRNAs. In other words, RNAi, unlike antisense, involves a catalytic-type reaction and degrades target mRNA in a non-stoichiometric manner. When administered to a cell or organism, exogenous dsRNA has been shown to direct the sequence-specific degradation of endogenous messenger RNA through RNAi. For example, Kreutzer, R., Limmer, S., International PCT Publication No. WO 00/44895 discloses dsRNAs that are effective agents for inducing RNAi, as well as methods for introducing dsRNA into a cell to inhibit the expression of a target gene. Tuschl et al., International PCT Publication No. WO 02/44321 report efficient cleavage of target RNA in a cell lysate using dsRNA having a 3'-nucleotide overhang, thus showing a correlation between the effectiveness of a dsRNA, its length, and the position and length of overhangs of unpaired nucleotides. WO 02/44321 reports improved efficiency when the 3'-nucleotide overhang is 2 nucleotides in length and when the unpaired nucleotide directly adjacent to the terminal nucleotide pair is a uridine base (i.e., a pyrimidine base).

While RNA interference using dsRNA has been shown to be an effective means for selective gene silencing, RNA is extremely unstable in some bodily fluids, particularly in serum. Thus, RNA, including dsRNA, can be degraded between the time it is administered to a subject and the time it enters a target cell. Even within the cell, RNA undergoes rapid degradation by nucleases. Although a more stable or nuclease resistant dsRNA would offer better bioavailability and hence improved effectiveness, the means known to date for stabilizing dsRNA against degradation are insufficient.

Thus, despite significant recent developments in the field of RNA interference, there remains a need for a more effective dsRNA molecule that can selectively and efficiently silence a target gene. More specifically, a dsRNA molecule having enhanced resistance to chemical and/or enzymatic degradation, and hence improved serum stability and bioavailability, and which can be readily and cost-effectively synthesized would be highly desirable. Compositions comprising such agents would be useful for treating diseases caused by abnormal expression or activity of a gene.

SUMMARY OF THE INVENTION

The invention relates to a double-stranded ribonucleic acid (dsRNA) having improved stability in cells and biological fluids, methods of identifying dsRNA having improved stability, as well as pharmaceutical compositions and methods for inhibiting the expression of a target gene in a cell using the dsRNA. The invention also relates to compositions and methods for treating diseases, maladies, or afflictions associated with the over- or under-expression of a target gene. The dsRNA of the invention comprises a nucleotide overhang of 1 to 4 nucleotides, and may further comprise at least one substituted or chemically modified nucleotide, such that the modified dsRNA has greater resistance to chemical or enzymatic digestion, and thus has increased stability and bioavailability than an identical dsRNA without the modification.

In one aspect, the invention relates to dsRNA having improved stability in cells and biological fluids, particularly serum. The dsRNA comprises two single strands. One strand of the dsRNA comprises a nucleotide sequence that is substantially identical to a portion of the target gene (the "sense" strand), and the other strand (the "complementary" or "antisense" strand) comprises a sequence that is substantially complementary to the target gene. The complementary RNA strand is less than 30 nucleotides, preferably less than 25 nucleotides in length, and more preferably 19 to 24 nucleotides in length. The complementary nucleotide sequence is preferably 20-23 nucleotides in length, and more preferably 22 nucleotides in length. The dsRNA of the present invention further comprises a single-stranded nucleotide overhang on at least one end of the dsRNA. In preferred embodiments, the nucleotide overhang comprises 1 to 4 unpaired nucleotides, wherein the unpaired nucleotide of the single-stranded overhang that is directly adjacent to the terminal nucleotide pair contains a purine base, and wherein the terminal nucleotide pair is a G-C pair, or wherein at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3' end of the complementary strand.

In another aspect, the invention relates to a pharmaceutical composition for inhibiting the expression of a target gene in an organism. The compositions comprise a dsRNA, as described above, and a pharmaceutically acceptable carrier. The pharmaceutically acceptable carrier may be an aqueous solution, such as phosphate buffered saline, or it may comprise a micellar structure, a liposome, a polymeric carrier, or release modifiers.

In yet another aspect, the invention relates to a method for inhibiting the expression of a target gene in a cell. The method comprises introducing a dsRNA, as described above, into the cell, and maintaining the cell for a time sufficient to obtain degradation of an mRNA transcript of the target gene. The cell may be a mammalian cell.

In yet a further aspect, the invention relates to a method for treating a disease, malady, or affliction caused by the expression of a target gene in a subject. The method comprises administering a pharmaceutical composition comprising a dsRNA, as described above, and a pharmaceutically acceptable carrier. The subject may be a human.

In another aspect, the invention relates to a method of identifying a dsRNA having increased stability in a biological sample. The method may comprise preparing a mixture of dsRNA, incubating the mixture of dsRNA in the biological sample, and identifying a dsRNA exhibiting an increased stability as compared to other dsRNA in the biological sample. The mixture of dsRNA may be prepared by chemical synthesis or by extraction from a biological sample. Alternatively, the method may comprise introducing a dsRNA into a cell, maintaining the cell under conditions suitable for expressing a protein encoded by a target gene, measuring an amount of the protein produced in the cell, comparing the amount of the protein produced in the cell to that in a control cell, and identifying a dsRNA that causes a reduction in the amount of protein in the cell as compared to the control cell. The cell may be a mammalian cell.

In still another aspect, the invention relates to a method of increasing the nuclease resistance of a dsRNA. The method comprises forming a dsRNA, as described above, wherein the nuclease resistance of the dsRNA is increased compared to a control composition.

The details of the invention are set forth in the accompanying drawings and the description below. Other features, objects, and advantages of the invention will be apparent from the description and drawings, and from the claims.

DETAILED DESCRIPTION OF THE INVENTION

Figure 1:
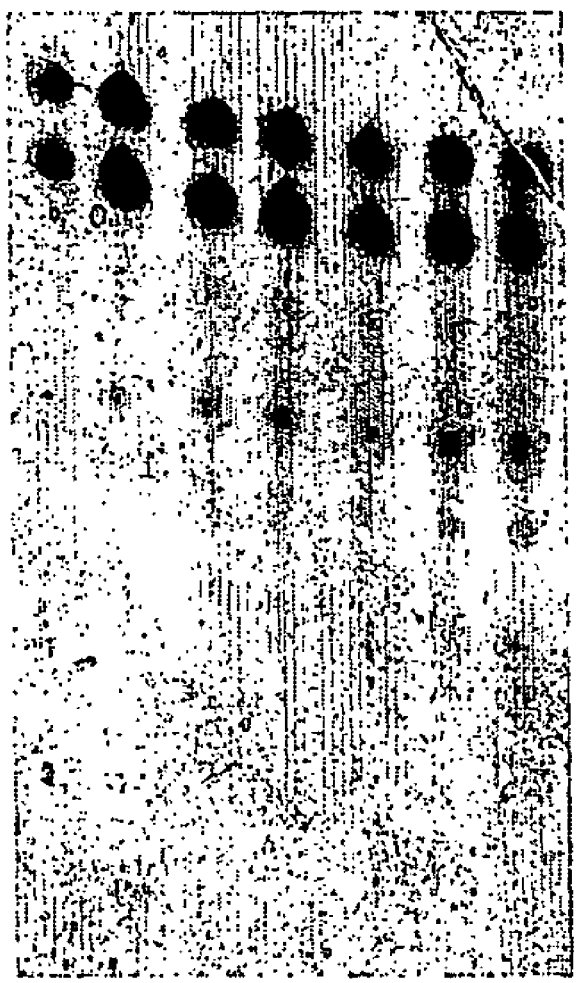
FIG. 1 is a gel electrophoretic separation of a dsRNA that is the subject of this invention without incubation, and after 0, 15, 30, 60, 120, and 240 minutes incubation in serum.

The present invention discloses modified double-stranded ribonucleic acid (dsRNA) having improved stability in cells and biological fluids compared to unmodified dsRNA recognizing the same target RNA, methods for the targeted selection of a dsRNA that comprises a single-stranded nucleotide overhang, methods of making a modified dsRNA, as well as compositions and methods for inhibiting the expression of a target gene in a cell or mammal using the modified dsRNA. The present invention also discloses compositions and methods for treating diseases in organisms caused by expression of a target gene using modified dsRNA. dsRNA directs the sequence-specific degradation of mRNA through a process known as RNA interference (RNAi). The process occurs in a wide variety of organisms, including mammals and other vertebrates.

The dsRNA of the invention comprises a complementary RNA strand and a sense RNA strand, wherein the complementary RNA strand has a nucleotide sequence which is substantially complementary to a target RNA, wherein at least one of the RNA strands comprises a nucleotide overhang of 1 to 4 nucleotides in length, and wherein the dsRNA may further comprise at least one chemically modified nucleotide. The inventors have demonstrated that dsRNA comprising a single-stranded overhang of 1 to 4 nucleotides in length, wherein the unpaired nucleotide of the single-stranded overhang that is directly adjacent to the terminal nucleotide pair contains a purine base, and wherein the last complementary nucleotide pairs on both ends of the dsRNA are a G-C pair, or, wherein at least two of the last four terminal nucleotide pairs are G-C pairs show increased stability, e.g. in standard measurements of melting points. The present inventors have also demonstrated that a dsRNA containing a chemically modified nucleotide has significantly improved serum stability compared to their unmodified dsRNA counterparts. The present invention encompasses these modified dsRNA and compositions comprising these dsRNAs and their use for specifically inactivating gene function. The use of modified dsRNA having improved resistance to enzymatic degradation (i.e., increased in vivo half-life), and hence improved bioavailability, facilitates the targeted degradation of mRNA of genes that are implicated in a wide variety of disease processes. Because of the increase stability and improved bioavailability of the modified dsRNA, less dsRNA is required to produce the desired RNA interference effect. Thus, the methods and compositions of the present invention comprising these modified dsRNA are useful for treating diseases and disorders caused by the expression or activity of a particular gene.

The following detailed description discloses how to make and use modified dsRNA and compositions containing modified dsRNA having improved serum stability to inhibit the expression of a target gene, as well as compositions and methods for treating diseases and disorders caused by the expression of the gene.

I. Definitions

For convenience, the meaning of certain terms and phrases used in the specification, examples, and appended claims, are provided below.

"G," "C," "A" and "U" each stand for a nucleotide that contains guanine, cytosine, adenine, and uracil as a base, respectively.

As used herein, "target gene" includes polynucleotides comprising a region that encodes a polypeptide or polynucleotide region that regulates replication, transcription, translation, or other process important in expression of the target protein or a polynucleotide comprising a region that encodes the target polypeptide and a region that regulates expression of the target polypeptide. Accordingly, the term "target gene" as used herein may refer to, for example, an mRNA molecule produced by the transcription of the gene of interest. Further, a "target gene" is a gene whose expression is to be selectively inhibited or silenced through RNA interference. The term "target gene" specifically encompasses any cellular gene or gene fragment whose expression or activity is associated with a disease or disorder (e.g., an oncogene), as well as any foreign or exogenous gene or gene fragment whose expression or activity is associated with a disease, such as a gene from a pathogenic organism (e.g., a viral or pro-viral gene, viroid, or *plasmodium*).

The term "complementary RNA strand" (also referred to herein as the "antisense strand") refers to the strand of a dsRNA that is substantially complementary to an RNA transcript that is formed during expression of the target gene, or its processing products (such as an mRNA), or a region (such as the 3'-UTR) of a (+) strand RNA virus or a portion thereof.

The term "sense strand," as used herein, refers to the strand of a dsRNA that is substantially identical to a portion of the target gene and is sufficiently complementary to the antisense strand to from a dsRNA under physiological conditions.

"dsRNA" refers to a ribonucleic acid molecule having a duplex structure comprising two complementary and antiparallel nucleic acid strands (i.e., the sense and antisense strands). Not all nucleotides of a dsRNA must exhibit Watson-Crick base pairs; the two RNA strands may be substantially complementary. The RNA strands may have the same or a different number of nucleotides. The complementary RNA strand has less than 30, preferably less than 25, and most preferably 19 to 24 nucleotides in length. The term "dsRNA" also includes "siRNA" or short interfering RNA.

It will be understood that the term "ribonucleotide" or "nucleotide" can, in the case of a modified RNA or nucleotide surrogate, also refer to a modified nucleotide, or surrogate replacement moiety at one or more positions. Thus, the dsRNA is or includes a region which is at least partially complementary to the target RNA. In certain embodiments, the dsRNA is fully complementary to the target RNA. It is not necessary that there be perfect complementarity between the dsRNA and the target, but the correspondence must be sufficient to enable the dsRNA, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments can include one or more but preferably 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be substantially complementary with the antisense strand to maintain the overall double-strand character of the molecule.

As used herein, "modified dsRNA" refers to a dsRNA molecule that comprises at least one alteration that renders it more resistant to nucleases (e.g., protein kinase) than an identical dsRNA molecule that recognizes the same target RNA. The modified dsRNA of the present invention include a single-stranded nucleotide overhang and/or at least one substituted nucleotide.

The term "substituted nucleotide" or "substituted base," as used herein, refer to a nucleotide or a nucleotide base which has been altered to render the dsRNA more resistant to nucleases (i.e., more stable) than a naturally occurring dsRNA or a chemically synthesized dsRNA that recognizes the same target sequence but lack the altered or additional nucleotide or nucleotide base. Exemplary modifications that generate substituted nucleotides that increase the stability of the dsRNA include, for example, replacing one nucleotide with another (e.g., replacing a nucleotide comprising a pyrimidine base with a nucleotide comprising a purine base, or replacing a wild-type nucleotide with a locked nucleotide), chemical modification of a base, chemical modification of a nucleotide (e.g., replacing a 2'-hydroxyl group with a chemical group, such as a 2'-amino- or a 2'-methyl group), and alteration of the 3' or 5' ends of an RNA strand of the dsRNA molecule (e.g., incorporating a non-nucleotide linkage, such as a propyl linker).

The terms "chemically modified base" or "chemically modified nucleotide base," as used herein, refer to a nucleotide base that has been chemically modified. The terms "unmodified base" or "unmodified nucleotide base" mean one of the naturally occurring or wild-type bases (adenine, cytosine, guanosine, uracil) joined to the 1' carbon of a pentose sugar, which has a phosphate bound to the 5' carbon. The term "chemically modified," as used herein, includes modifications that introduce chemical moieties or other structural features that differ from those seen in naturally occurring RNA. Such modifications may affect the ability of a base to hydrogen bond with its normal complementary base, and include, without limitation, heterocyclic derivatives, nucleotide analogs, covalent modifications such as the introduction of modified nucleotides, or the inclusion of pendant groups that are not naturally found in RNA molecules. A "chemically modified nucleotide," as used herein, means a nucleotide that contains a modification in its chemical structure that produces a measurable change in stability of a dsRNA containing a modified nucleotide than an identical dsRNA without the modified nucleotide.

The terms "purine" and "purine base" refer to the naturally occurring adenine and guanine bases. The terms also refer to modifications of these bases such as bases substituted at the 8-position, or guanine analogs modified at the 6-position or the analog of adenine, 2-amino or 2-methyl purine, as well as analogs of purines having carbon replacing nitrogen at the 9-position, such as 9-deaza purine derivatives and other purine analogs.

As used herein, a "nucleotide overhang" refers to the unpaired nucleotide or nucleotides that protrude from the duplex structure when a 3'-end of one RNA strand extends beyond the 5'-end of the other complementary strand, or vice versa. "Blunt" or "blunt end" means that there are no unpaired nucleotides at that end of the dsRNA, i.e., no nucleotide overhang. A "blunt ended" dsRNA is a dsRNA that is double stranded over its entire length, i.e., no nucleotide overhang at either end of the molecule.

The term "double-stranded" means two separate RNA strands comprising a region in which at least a portion of the strands are sufficiently complementary to hydrogen bond and form a duplex structure. The term "duplex" or "duplex structure" refers to the region of the dsRNA molecule wherein the two separate RNA strands are substantially complementary, and thus hybridize to each other.

The term "terminal base pair," as used herein, refers to the last nucleotide base pair on one end of the duplex region of the dsRNA. Thus, where the dsRNA is blunt ended (i.e., has no nucleotide overhangs), the last nucleotide base pairs at both ends of the dsRNA are terminal base pairs. Where a dsRNA has a nucleotide overhang at one or both ends of the duplex structure, the last nucleotide base pair(s) immediately adjacent the nucleotide overhang(s) is the terminal base pair at that end(s) of the dsRNA.

The term "silence" means to at least partially suppress. For example, in certain instances, the gene is suppressed by at least about 25%, 35%, or 50% by administration of the double-stranded oligonucleotide of the invention. In a preferred embodiment, the gene is suppressed by at least about 60%, 70%, or 80% by administration of the double-stranded oligonucleotide of the invention. In a more preferred embodiment, the gene is suppressed by at least about 85%, 90%, or 95% by administration of the double-stranded oligonucleotide of the invention. In a most preferred embodiment, the gene is suppressed by at least about 98% or 99% by administration of the double-stranded oligonucleotide of the invention II. Double-Stranded Ribonucleic Acid (dsRNA)

In one embodiment, the invention relates to a double-stranded ribonucleic acid (dsRNA) having improved resistance to chemical and/or nuclease digestion, and thus increased serum stability and a longer in vivo half-life. Increasing the in vivo half-life of the dsRNA results in enhanced bioavailability, and hence enhanced effectiveness in inhibiting expression or activity of a target gene (Czauderna et al., NAR 2003, 31:2705-2716). In the blood, the stability of dsRNA is determined by its susceptibility to degradation by enzymes present in the blood. Surprisingly, it has been shown that the susceptibility to degradation is dependent on the sequences of the single strands that form the dsRNA. Thus, the present invention is based, at least in part, on improving the efficiency of dsRNA as a therapeutic agent, by increasing the serum stability of the dsRNA, while maintaining the ability of the dsRNA to mediate RNA interference in vivo. In certain instances, serum stability refers to a measurement of stability in blood that is approximated experimentally by determining the stability in serum (i.e., the aqueous phase of blood free of cellular components and coagulation factors).

The dsRNA of the present invention comprises two single strands. One strand of the dsRNA comprises a nucleotide sequence that is substantially identical to a portion of the target gene (the "sense" strand), and the other strand (the "complementary" or "antisense" strand) comprises a sequence that is substantially complementary to a portion of an RNA transcript that is formed during expression of the target gene. The strands are sufficiently complementary to hybridize to form a duplex structure. The complementary RNA strand is less than 30 nucleotides, preferably less than 25 nucleotides in length, and more preferably 19 to 24 nucleotides in length. The complementary nucleotide sequence is preferably 20-23 nucleotides in length, and more preferably 22 nucleotides in length. The dsRNA of the present invention further comprise at least one single-stranded nucleotide overhang, wherein the unpaired nucleotide of the single-stranded overhang that is directly adjacent to the terminal nucleotide pair contains a purine base, and wherein the terminal nucleotide pair is a G-C pair, or wherein at least two of the last four complementary nucleotide pairs are G-C pairs. The dsRNA of the present invention may further comprise a substituted or chemically modified nucleotide. As discussed in detail in Section III below, the dsRNA can be synthesized by standard methods known in the art, e.g., using an automated DNA synthesizer, such as those commercially available from Biosearch, Applied Biosystems, Inc.

In one embodiment of the invention, at least one end of the dsRNA comprises a single-stranded nucleotide overhang. A single-stranded overhang in the dsRNA contributes to an increase in the intracellular effectiveness of the dsRNA and thus have superior inhibitory properties compared with their blunt-ended counterparts. However, dsRNA with at least one blunt end show greater in vivo stability (i.e., it is more resistant to degradation in the blood, plasma, and cells) than dsRNA with overhangs at both ends. The presence of only one overhang strengthens the interference activity of the dsRNA. Further, dsRNA having only one overhang has proven particularly effective in vivo (as well as in a variety of cells, and culture mediums), and are more stable than dsRNA having two blunt ends. In theory, the singled-stranded overhang may comprise any number of nucleotides. In certain embodiments, the single-stranded overhang may be less than or equal to 15 nucleotides in length. In certain preferred embodiments, the single-stranded overhang is 1 to 4 nucleotides. In other preferred embodiments, the single-stranded overhang is 1 or 2 nucleotides.

Remarkably, the presence of a purine base on the nucleotide overhang immediately adjacent to the terminal base pair provides further resistance to degradation. Thus, in another embodiment, the unpaired nucleotide directly adjacent to the terminal nucleotide pair comprises a purine base, such as guanine (G) or adenine (A). When a single-strand overhang consists of more than one nucleotide, stability is further increased when at least half of the overhang consists of purine bases, in particular G or A bases. In an exemplary embodiment, the overhang comprises the sequence 5'-GC-3'. Further, when the nucleotide overhang is 2 nucleotides in length, the sequence is preferably 5'-GC-3'. This contradicts the finding of WO 02/44321, which reports that in a 2 nucleotide overhang at the 3'-end of a dsRNA, uridine (i.e., a pyrimidine) is preferable as the unpaired nucleotide that is directly adjacent to the terminal nucleotide pair.

In a further embodiment, the single-stranded overhang is located at the 3'-end of the complementary (antisense) RNA strand. In a still further embodiment, the nucleotide overhang is at the 3'-end of the complementary RNA strand, and the 5'-end is blunt.

The present invention is based, in part, on the discovery that small changes in the extent of base-pairing or hydrogen bonding between the two RNA strands can have a significant effect on the stability of the dsRNA. Moreover, the present inventors have determined that a subtle alteration in the extent of hydrogen bonding between the two RNA strands, and particularly the placement of the modification, can be used to improve the stability of the dsRNA as compared to an otherwise identical (but unmodified) dsRNA. Thus, for example, an adenosine-uracil (A-U) base pair c an be replaced with a guanine-cytosine (G-C) base pair to increase the hydrogen bonding interaction between the two RNA strands. The potential for dissociation between the RNA strands is thereby reduced, due to the additional hydrogen bond (three in G-C as compared to two in A-U), thereby improving the stability of the dsRNA molecule.

In one embodiment, the nucleotides comprising adenine (A) and uracil (U) in at least one nucleotide base pair of a wild-type or unmodified dsRNA is replaced with nucleotides comprising guanine (G) and cytosine (C) to form a G-C base pair having increased hydrogen bonding. Preferably, the base modification is introduced in a terminal base pair at one end of the duplex structure, and, more preferably, in the terminal base pairs at both ends of the duplex structure. Thus, in a preferred embodiment, the dsRNA comprises a G-C pair as the terminal nucleotide pair on both ends of the duplex structure. In an alternate embodiment, the dsRNA comprises at least two G-C pairs within the last four terminal nucleotide pairs (i.e., the last four contiguous nucleotide base pairs on both ends of the duplex structure).

In the present invention, a method is provided for the targeted selection of a dsRNA consisting of two single strands that exhibits increased effectiveness in inhibiting the expression of a target gene by means of RNA interference, wherein the sequence of the single strands of the dsRNA are selected such that they comprise at least one single-stranded overhang of 1 to 4 unpaired nucleotides; wherein the unpaired nucleotide directly adjacent to the terminal base pair is a purine base; and wherein the terminal nucleotide pair is a G-C pair, or at least two of the last four terminal nucleotide pairs are G-C pairs.

The sequences of the single strands of the dsRNA can be selected by selecting a region and its length within the target gene to be inhibited, such that a dsRNA with a strand that is complementary exhibit the above-described elements. Because single nucleotides that are not complementary to the target gene do not inhibit RNA interference, it is possible to attach a single nucleotide or single nucleotides to the region of a strand of dsRNA that is complementary to the target gene, or to replace individual nucleotides in the strand in order to obtain a dsRNA that exhibits the elements defined in the terms of the invention.

Table 1 shows exemplary dsRNA having increased RNA stability, and which share certain common structural features. The dsRNA of Table 1 are provided for illustration only, and are not intended to limit the scope of the invention. Any dsRNA having increased stability due to one or more of these structural features is encompassed by the present invention. For example, the dsRNA of Table 1 comprise all of the above-discussed structural features, specifically (1) a 1-2 nucleotide overhang at one end and a blunt end at the other; (2) the unpaired nucleotide adjacent to the terminal nucleotide base pair is a purine; and (3) the terminal base pairs at both ends of the dsRNA are G-C pairs, or at least two of the four consecutive terminal base pairs at both ends are G-C base pairs.

TABLE 1

| Source | Sequence Information |
| --- | --- |
| From Bcl-2 | 5'-GGCGACUUCGCCGAGAUGUCC-3' (SEQ ID NO: 7)<br>3'-CGCCGCUGAAGCGGCUCUACAGG-5' (SEQ ID NO: 8) |
| From Bcl-2 | 5'-ACCGGGCAUCUUCUCCUCCCA-3' (SEQ ID NO: 9)<br>3'-CGUGGCCCGUAGAAGAGGAGGGU-5' (SEQ ID NO: 10) |

Table 2 represents a list of dsRNA molecules whose sequences are known, and that satisfy the structural requirements of a dsRNA as described herein. dsRNA molecules identified by SEQ ID NOS: 1, 2, 3, 4, 5, 6, 13, 14, 15, and 16 in Table 2 have not been modified, i.e., none of these dsRNA molecules comprise a nucleotide or a nucleotide base which has been altered or added to the sequence to render the molecule more resistant to nucleases. dsRNA represented by SEQ ID NOS: 17 and 18 was described in WO 02/44321 and WO 03/099298. Nevertheless, each of these six dsRNA molecules are expressly excluded from the scope of the present invention.

TABLE 2

| Sequence Information | |
| --- | --- |
| 5'-CAGGACCUCGCCGCUGCAGACC-3' | (SEQ ID NO: 1) |
| 3'-CGGUCCUGGAGCGGCGACGUCUGG-5' | (SEQ ID NO: 2) |
| 5'-GCCUUUGUGGAACUGUACGGCC-3' | (SEQ ID NO: 3) |
| 3'-UACGGAAACACCUUGACAUGCCGG-5' | (SEQ ID NO: 4) |
| 5'-CUUCUCCGCCUGACACCGCUGCAA-3' | (SEQ ID NO: 5) |
| 3'-GAAGAGGCGGAGUGUGGCGACG-5' | (SEQ ID NO: 6) |
| 5'-ACGGCUAGCUGUGAAAGGUCC-3' | (SEQ ID NO: 13) |

TABLE 2-continued

| Sequence Information | |
| --- | --- |
| 3'-AGUGCCGAUCGACACUUUCCAGG-5' | (SEQ ID NO: 14) |
| 5'-CAAGGAGCAGGGACAAGUUAC-3' | (SEQ ID NO: 15) |
| 3'-AAGUUCCUCGUCCCUGUUCAAUG-5' | (SEQ ID NO: 16) |
| 5'-CACGUACGCGGAAUACUUCGAAA-3' | (SEQ ID NO: 17) |
| 3'-GUGCAUGCGCCUUAUGAAGCU-5' | (SEQ ID NO: 18) |

Table 3 represents a list of dsRNA molecules wherein both ends comprise single-stranded nucleotide overhangs whose sequences are known, and that satisfy the structural requirements of a dsRNA as described herein. The dsRNA represented by SEQ ID NOS: 19 and 20 was described in WO 04/011647, and the dsRNAs represented by SEQ ID NOS: 21-42 were described in WO 03/012052. Nevertheless, each of these 12 dsRNA molecules are expressly excluded from the scope of the present invention.

TABLE 3

| Sequence Information | Target Gene Name |
| --- | --- |
| 5'-CCGCUUGACUGCAGAGAGUGC-3' (SEQ ID NO: 19)<br>3'-UCGGCGAACUGACGUCUCUCA-5' (SEQ ID NO: 20) | HCV-specific |
| 5'-CAUCUUCUUCAAGGACGACGGC-3' (SEQ ID NO: 21)<br>3'-UGGUAGAAGAAGUUCCUGCUGC-5' (SEQ ID NO: 22) | green fluorescent protein (egfP) |
| 5'-GGUGGCGCUGGAUGGUAAGCCGC-3' (SEQ ID NO: 23)<br>3'-UACCACCGCGACCUACCAUUCGG-5' (SEQ ID NO: 24) | LacZ |
| 5'-UCCCCAGGAGGCCUGCGGGAGC-3' (SEQ ID NO: 25)<br>3'-GGAGGGGUCCUCCGGACGCCCU-5' (SEQ ID NO: 26) | human Erb-B2 (Her2) |
| 5'-UGCAGCUUCGAAGCCUCACAGA-3' (SEQ ID NO: 27)<br>3'-CGACGUCGAAGCUUCGGAGUGU-5' (SEQ ID NO: 28) | human Erb-B2 (Her2) |
| 5'-UGGGGAGAGAGUUCUGAGGAUU-3' (SEQ ID NO: 29)<br>3'-CGACCCCUCUCUCAAGACUCCU-5' (SEQ ID NO: 30) | human Erb-B2 (Her2) |
| 5'-ACCUCCGCAACAACUACGCGC-3' (SEQ ID NO: 31)<br>3'-GAUGGAGGCGUUGUUGAUGCG-5' (SEQ ID NO: 32) | PNMT |
| 5'-GUAGACCUUGCUACUGCCUGC-3' (SEQ ID NO: 33)<br>3'-ACCAUCUGGAACGAUGACGGA-5' (SEQ ID NO: 34) | RAd51C |
| 5'-CAUGACGGAACUAGAGACAGC-3' (SEQ ID NO: 35)<br>3'-UGGUACUGCCUUUGAUCUCUGU-5' (SEQ ID NO: 36) | S100P |
| 5'-CUCUACGCUUGUACGAGGAGC-3' (SEQ ID NO: 37)<br>3'-CAGAGAUGCGAACAUGCUCCU-5' (SEQ ID NO: 38) | TBX2 |
| 5'-CAGACUUCGGAGUACCUGCGC-3' | TXNIP |

TABLE 3-continued

| Sequence Information | Target Gene Name |
|---|---|
| (SEQ ID NO: 39)<br>3'-UUGUCUGAAGCCUCAUGGACG-5'<br>(SEQ ID NO: 40) | |
| 5'-CAUCUUCUUCAAGGACGACGGC-3'<br>(SEQ ID NO: 41)<br>3'-UGGUAGAAGAAGUUCCUGCUGC-5'<br>(SEQ ID NO: 42) | green fluorescent<br>protein (egfP) |

In another embodiment, the present invention provides dsRNA having nucleotide sequences that are substantially identical or complementary to at least a portion of a target gene. 100% sequence identity between the sense strand of the inhibitory dsRNA and the portion of the target gene is typically preferred. However, modified dsRNA having at least 70%, or 85%, or 90% or 95% sequence identity to the target gene, as well as improved resistance to enzymatic degradation and/or dissociation, are encompassed by the present invention. In a particularly preferred embodiment, the modified dsRNA has the following structural features: (1) a nucleotide overhang at one end of the dsRNA and a blunt end at the other end; (2) the unpaired nucleotide on the nucleotide overhang adjacent to the terminal base pair comprises a purine base; and (3) the terminal base pairs on both ends of the duplex structure are G-C base pairs, or at least two of the four consecutive terminal base pairs on both ends are G-C base pairs. Such modified dsRNA have improved stability in biological tissues, thus allowing administration at low dosages, i.e., less than 5 mg/kg body weight of the recipient per day. Preferably, the complementary strand of the modified dsDNA has a nucleotide overhang at the 3'-end, and the 5'-end is blunt.

In yet another embodiment, the dsRNA is chemically modified to further enhance stability. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, Biochem. (1996) 35:14665-14670). In a particular embodiment, the 5'-end of the complementary (antisense) RNA strand and the 3'-end of the sense RNA strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds.

In certain embodiments, a chemical bond may be formed by means of one or several bonding groups, wherein such bonding groups are preferably poly-(oxyphosphinicooxy-1, 3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light. In certain instances, partially self-associated single-strands (stem loops) are excluded.

In yet another embodiment, the nucleotides at one or both of the two single strands may be modified to prevent or inhibit the activation of cellular enzymes, such as a protein kinase, whose activation is dependent on dsRNA. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, preferably by a 2'-amino or a 2'-methyl group. Also, at least one nucleotide may be modified to form a locked nucleotide. Such locked nucleotide contains a methylene bridge that connects the 2'-oxygen of ribose with the 4'-carbon of ribose. Oligonucleotides containing the locked nucleotide are described in Koshkin, A. A., et al., *Tetrahedron* (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

Conjugating a ligand to a dsRNA can enhance its cellular absorption. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of an dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the present invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the present invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated dsRNA and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the present invention include, but are not limited to, 2'-aminoalkoxy-5'-ODMT-nucleosides, 2'-6-aminoalkylamino-5'-ODMT-nucleosides, 5'-6-aminoalkoxy-2'-deoxy-nucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.,* 1994, 35:7821; Verhart and Tesser, *Rec. Trav. Chim. Pays-Bas,* 1987, 107:621).

Additional amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in solid-phase Synthesis*, 3rd *International Symposium,* 1994, Ed. Roger Epton, Mayflower Worldwide, 115-[24]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the present invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the present invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111;

5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497.

Some preferred embodiments of the present invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the present invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering,* pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,808,027; all of which are hereby incorporated by reference.

In certain embodiments, the oligonucleotides employed in the ligand-conjugated oligonucleotides of the present invention may additionally or alternatively comprise one or more substituted sugar moieties. Preferred oligonucleotides comprise one of the following at the 2' position: OH; F; O—, S—, or N-alkyl, O—, S—, or N-alkenyl, or O, S—or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_nO]_mCH_3$, O$(CH_2)_nOCH_3$, O$(CH_2)_nNH_2$, O$(CH_2)_nCH_3$, O$(CH_2)_nONH_2$, and O$(CH_2)_n$ON[$(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy[2'-O—$CH_2CH_2OCH_3$, also known as 2'-O-(2-methoxyethyl) or 2'-MOE] (Martin et al., *Helv. Chim. Acta,* 1995, 78, 486), i.e., an alkoxyalkoxy group. a further preferred modification includes 2'-dimethylaminooxyethoxy, i.e., a O$(CH_2)_2$ON$(CH_3)_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)$_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (*J. Org. Chem.* 1991, 56:4329); and Delgardo et. al. (*Critical Reviews in Therapeutic Drug Carrier Systems* 1992, 9:249), each of which is hereby incorporated by reference in its entirety. Further sugar modifications are disclosed by Cook (*Anti-Cancer Drug Design*, 1991, 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-NR$_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.*, 1997, 62:3415-3420). 2'-NR nucleosides are disclosed by Goettingen, M., *J. Org. Chem.*, 1996, 61, 6273-6281; and Polushin et al., *Tetrahedron Lett.*, 1996, 37, 3227-3230. Further representative 2'-substituent groups amenable to the present invention include those having one of formula I or II:

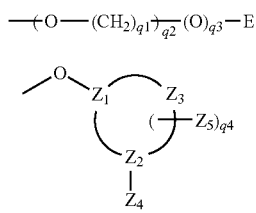

wherein,

E is C$_1$-C$_{10}$ alkyl, N(Q$_3$)(Q$_4$) or N=C(Q$_3$)(Q$_4$); each Q$_3$ and Q$_4$ is, independently, H, C$_1$-C$_{10}$ alkyl, dialkylaminoalkyl, a nitrogen protecting group, a tethered or untethered conjugate group, a linker to a solid support; or Q$_3$ and Q$_4$, together, form a nitrogen protecting group or a ring structure optionally including at least one additional heteroatom selected from N and O;

q$_1$ is an integer from 1 to 10;

q$_2$ is an integer from 1 to 10;

q$_3$ is 0 or 1;

q$_4$ is 0, 1 or 2;

each Z$_1$, Z$_2$ and Z$_3$ is, independently, C$_4$-C$_7$ cycloalkyl, C$_5$-C$_{14}$ aryl or C$_3$-C$_{15}$ heterocyclyl, wherein the heteroatom in said heterocyclyl group is selected from oxygen, nitrogen and sulfur;

Z$_4$ is OM$_1$, SM$_1$, or N(M$_1$)$_2$; each M$_1$ is, independently, H, C$_1$-C$_8$ alkyl, C$_1$-C$_8$ haloalkyl, C(=NH)N(H)M$_2$, C(=O)N(H)M$_2$ or OC(=O)N(H)M$_2$; M$_2$ is H or C$_1$-C$_8$ alkyl; and Z$_5$ is C$_1$-C$_{10}$ alkyl, C$_1$-C$_{10}$ haloalkyl, C$_2$-C$_{10}$ alkenyl, C$_2$-C$_{10}$ alkynyl, C$_6$-C$_{14}$ aryl, N(Q$_3$)(Q$_4$), OQ$_3$, halo, SQ$_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring 0 include, but are not limited to, S, CH$_2$, CHF, and CF$_2$. See, e.g., Secrist et al., Abstract 21, *Program & Abstracts, Tenth International Roundtable, Nucleosides, Nucleotides and their Biological Applications*, Park City, Utah, Sep. 16-20, 1992.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-5-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., dihexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Representative United States patents relating to the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521, 302).

Alternatively, the molecule being conjugated may be converted into a building block, such as a phosphoramidite, via an alcohol group present in the molecule or by attachment of a linker bearing an alcohol group that may be phosphitylated.

Importantly, each of these approaches may be used for the synthesis of ligand conjugated oligonucleotides. Amino-linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

III. Method of Making Modified dsRNA Having Improved Stability

The invention further relates to a method for making a dsRNA having improved serum stability and hence improved bioavailability. The modified dsRNA of the invention can be isolated from cells, produced from a DNA template, or can be chemically synthesized using methods known in the art prior to alteration using the methods of the invention.

In one embodiment, the modified dsRNA are chemically synthesized. The method comprises synthesizing a complementary RNA strand and a sense RNA strand, wherein at least one of the RNA strands comprises a single-stranded nucleotide overhang and may further comprise a substituted nucleotide, and mixing the two RNA strands to form a dsRNA. The nucleotide sequences of the individual RNA strands are selected such that one of the two strands has a region of complementarity to the target gene to be inhibited (i.e., the complementary RNA strand comprises a nucleotide sequence that is complementary to a region of an mRNA transcript that is formed during expression of the target gene, or its processing products, or a region of a (+) strand virus). The nucleotide sequence is then modified for improved stability by replacing or adding a nucleotide(s) in accordance with the present invention. Also, the RNA strand(s) can be further chemically modified as described herein. The step of synthesizing the RNA strand preferably involves solid-phase synthesis, wherein individual nucleotides are joined end to end through the formation of internucleotide 3'-5' phosphodiester bonds in consecutive synthesis cycles.

In general, the oligonucleotides of the present invention can be synthesized using protocols known in the art, for example, as described in Caruthers, et al., *Methods in Enzymology* (1992) 211:3-19; Thompson, et al., International PCT Publication No. WO 99/54459; Wincott, et al., *Nucl. Acids Res.* (1995) 23:2677-2684; Wincott, et al., *Methods Mol. Bio.*, (1997) 74:59; Brennan, et al., *Biotechnol. Bioeng.* (1998) 61:33-45; and Brennan, U.S. Pat. No. 6,001,311; each of which is hereby incorporated by reference in its entirety herein. In general, the synthesis of oligonucleotides involves conventional nucleic acid protecting and coupling groups, such as dimethoxytrityl at the 5'-end, and phosphoramidites at the 3'-end. In a non-limiting example, small scale syntheses are conducted on a Expedite 8909 RNA synthesizer sold by Applied Biosystems, Inc. (Weiterstadt, Germany), using ribonucleoside phosphoramidites sold by ChemGenes Corporation (Ashland Technology Center, 200 Homer Avenue, Ashland, Mass. 01721, USA). Alternatively, syntheses can be performed on a 96-well plate synthesizer, such as the instrument produced by Protogene (Palo Alto, Calif., USA), or by methods such as those described in Usman, et al., *J. Am. Chem. Soc.* (1987) 109:7845; Scaringe, et al., *Nucl. Acids Res.* (1990) 18:5433; Wincott, et al., *Nucl. Acids Res.* (1990) 23:2677-2684; and Wincott, et al., *Methods Mol. Bio.* (1997) 74:59, each of which is hereby incorporated by reference in its entirety.

The nucleic acid molecules of the present invention may be synthesized separately and joined together post-synthetically, for example, by ligation (Moore, et al., *Science* (1992) 256: 9923; Draper, et al., International PCT publication No. WO 93/23569; Shabarova, et al., *Nucl. Acids Res.* (1991) 19:4247; Bellon, et al., *Nucleosides & Nucleotides* (1997) 16:951; and Bellon, et al., *Bioconjugate Chem.* (1997) 8:204; or by hybridization following synthesis and/or deprotection. The nucleic acid molecules can be purified by gel electrophoresis using conventional methods or can be purified by high pressure liquid chromatography (HPLC; see Wincott et al., supra, the totality of which is hereby incorporated herein by reference) and re-suspended in water.

In one embodiment, the method of making modified dsRNA comprises increasing the number of G-C base pairs in the dsRNA, particularly in the terminal nucleotide base pairs or in the four consecutive terminal nucleotide base pairs, to increase hydrogen bonding interaction between the two RNA strands. In this embodiment, wild-type nucleotides containing A and U bases are replaced with nucleotides containing G and C bases during the synthetic process. Alternatively or in addition, additional nucleotides containing G and C bases may be inserted during the synthetic process so as to produce appropriately placed G-C base pairs, i.e., positioned to form a terminal nucleotide G-C base pair or to produce G-C base pairs within the four consecutive terminal nucleotides of the duplex structure.

In yet another embodiment, the method comprises substituting or adding a nucleotide containing a purine base at the first unpaired nucleotide immediately adjacent to the terminal base pairs of the duplex structure. In this embodiment, a nucleotide comprising a purine base is substituted for a nucleotide containing a pyrimidine base, or the purine nucleotide is inserted into the sequence adjacent to the terminal base pair.

In another embodiment, at least one nucleotide of the dsRNA is chemically modified to introduce chemical moieties or other structural features that differ from those seen in naturally occurring RNA. Such modifications may affect the ability of a base to hydrogen bond with its normal complementary base, and include, without limitation, heterocyclic derivatives, nucleotide analogs, covalent modifications such as the introduction of modified nucleotides, or the inclusion of pendant groups that are not naturally found in RNA molecules. Exemplary modifications and methods for introducing such modifications into dsRNA are known in the art, including those modification and methods discussed in Section II above and the references cited therein.

In other embodiments, dsRNA is isolated from cells or produced from a DNA template prior to alteration using methods known in the art. In these alternate embodiments, the stability of the dsRNA can be increased prior to use by any of a number of well-known techniques, including those discussed above.

IV. Pharmaceutical Compositions Comprising dsRNA

In one embodiment, the invention relates to a pharmaceutical composition comprising a modified dsRNA, as described in the preceding sections, and a pharmaceutically acceptable carrier, as described below. The pharmaceutical composition comprising the modified dsRNA is useful for treating a disease caused by expression of a target gene. In this aspect of the invention, the dsRNA of the invention is formulated as described below. The pharmaceutical composition is administered in a dosage sufficient to inhibit expression of the target gene.

The skilled artisan will appreciate that certain factors may influence the dosage and timing required to effectively treat a subject, including but not limited to the severity of the infection or disease, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNA encompassed by the invention can be made using conventional methodologies or on the basis of in vivo testing using an appropriate animal model, as described elsewhere herein.

Advances in mouse genetics have generated a number of mouse models for the study of various human diseases. For example, mouse repositories can be found at The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

Toxicity and therapeutic efficacy of dsRNA can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. dsDNAs which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any dsDNA used in the method of the invention, the therapeutically effective dose can be estimated initially from cell culture assays. A dose may be formulated in animal models to achieve a circulating plasma concentration range of the dsDNA or, when appropriate, of the polypeptide product of a target sequence (e.g., achieving a decreased concentration of the polypeptide) that includes the IC50 (i.e., the concentration of the test dsDNA which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNA useful according to the invention can be administered in combination with other known agents effective in treating viral infections and diseases. In any event, the administering physician can adjust the amount and timing of dsRNA administration on the basis of results observed using standard measures of efficacy known in the art or described herein.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration.

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce dsRNA into cell cultures, surprisingly these methods and agents are not necessary for uptake of dsRNA in vivo. The dsRNA of the present invention are particularly advantageous in that they do not require the use of an auxiliary agent to mediate uptake of the dsRNA into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated gene-silencing effects, will range from about 0.0001 to about 100 mg per kilogram of body weight per day.

In general, a suitable dose of dsRNA will be in the range of 0.01 to 5.0 milligrams per kilogram body weight of the recipient per day, preferably in the range of 0.1 to 2.5 milligrams per kilogram body weight of the recipient per day, more preferably in the range of 0.1 to 200 micrograms per kilogram body weight per day, and most preferably in the range of 0.1 to 100 micrograms per kilogram body weight per day. The pharmaceutical composition may be administered once per day, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals, such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups, such as cyanoacrylates and methacrylates).

V. Methods for Treating Diseases Caused by Expression of a Target Gene

In one embodiment, the invention relates to a method for treating a subject having a disease or at risk of developing a disease caused by the expression of a target gene. In this embodiment, the modified dsRNA of the invention may act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., human), such that expression of the target gene is silenced. Because of their high efficiency and specificity, the dsRNA of the present invention specifically target mRNA of target genes of diseased cells and tissues, as described below, and at low dosages.

Examples of genes which can be targeted for treatment include, without limitation, an oncogene (Hanahan, D. and R. A. Weinberg, *Cell* (2000) 100:57; and Yokota, J., *Carcinogenesis* (2000) 21(3):497-503); a cytokine gene (Rubinstein, M., et al., *Cytokine Growth Factor Rev.* (1998) 9(2):175-81); an idiotype (Id) protein gene (Benezra, R., et al., *Oncogene* (2001) 20(58):8334-41; Norton, J. D., *J. Cell Sci.* (2000) 113(22):3897-905); a prion gene (Prusiner, S. B., et al., *Cell* (1998) 93(3):337-48; Safar, J., and S. B. Prusiner, *Prog. Brain Res.* (1998) 117:421-34); a gene that expresses molecules that induce angiogenesis (Gould, V. E. and B. M. Wagner, *Hum. Pathol.* (2002) 33(11):1061-3); adhesion molecules (Chothia, C. and E. Y. Jones, *Annu. Rev. Biochem.* (1997) 66:823-62; Parise, L. V., et al., *Semin. Cancer Biol.* (2000) 10(6):407-14); cell surface receptors (Deller, M. C., and Y. E. Jones, *Curr. Opin. Struct. Biol.* (2000) 10(2):213-9); genes of proteins that are involved in metastasizing and/or invasive processes (Boyd, D., *Cancer Metastasis Rev.* (1996) 15(1):77-89; Yokota, J., *Carcinogenesis* (2000) 21(3):497-503); genes of proteases as well as of molecules that regulate apoptosis and the cell cycle (Matrisian, L. M., *Curr. Biol.* (1999) 9(20): R776-8; Krepela, E., *Neoplasma* (2001) 48(5):332-49; Basbaum and Werb, *Curr. Opin. Cell Biol.* (1996) 8:731-738; Birkedal-Hansen, et al., *Crit. Rev. Oral Biol. Med.* (1993) 4:197-250; Mignatti and Rifkin, *Physiol. Rev.* (1993) 73:161-195; Stetler-Stevenson, et al., *Annu. Rev. Cell Biol.* (1993) 9:541-573; Brinkerhoff, E., and L. M. Matrisan, *Nature Reviews* (2002) 3:207-214; Strasser, A., et al., *Annu. Rev. Biochem.* (2000) 69:217-45; Chao, D. T. and S. J. Korsmeyer, *Annu. Rev. Immunol.* (1998) 16:395-419; Mullauer, L., et al., *Mutat. Res.* (2001) 488(3):211-31; Fotedar, R., et al., *Prog. Cell Cycle Res.* (1996) 2:147-63; Reed, J. C., *Am. J. Pathol.* (2000) 157(5):1415-30; D'Ari, R., *Bioassays* (2001) 23(7): 563-5); genes that express the EGF receptor; Mendelsohn, J. and J. Baselga, *Oncogene* (2000) 19(56):6550-65; Normanno, N., et al., *Front. Biosci.* (2001) 6:D685-707); and the multi-drug resistance 1 gene, MDR1 gene (Childs, S., and V. Ling, *Imp. Adv. Oncol.* (1994) 21-36).

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

One aspect of the invention relates to a method of treating a subject at risk for or afflicted with unwanted cell proliferation, e.g., malignant or nonmalignant cell proliferation. The method comprises providing an dsRNA, wherein the dsRNA can inhibit by RNA interference, a gene which promotes unwanted cell proliferation; and administering a therapeutically effective dose of the dsRNA to a subject, preferably a human subject.

In a preferred embodiment the gene is a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In a preferred embodiment the dsRNA silences the PDGF beta gene, and thus can be used to treat a subject having or at risk for a disorder characterized by unwanted PDGF beta expression, e.g., testicular and lung cancers.

In another preferred embodiment the dsRNA silences the Erb-B gene, and thus can be used to treat a subject having or at risk for a disorder characterized by unwanted Erb-B expression, e.g., breast cancer.

In a preferred embodiment the dsRNA silences the Src gene, and thus can be used to treat a subject having or at risk for a disorder characterized by unwanted Src expression, e.g., colon cancers.

In a preferred embodiment the dsRNA silences the CRK gene, and thus can be used to treat a subject having or at risk for a disorder characterized by unwanted CRK expression, e.g., colon and lung cancers.

In a preferred embodiment the dsRNA silences the GRB2 gene, and thus can be used to treat a subject having or at risk for a disorder characterized by unwanted GRB2 expression, e.g., squamous cell carcinoma.

In another preferred embodiment the dsRNA silences the RAS gene, and thus can be used to treat a subject having or at risk for a disorder characterized by unwanted RAS expression, e.g., pancreatic, colon and lung cancers, and chronic leukemia.

In another preferred embodiment the dsRNA silences the MEKK gene, and thus can be used to treat a subject having or at risk for a disorder characterized by unwanted MEKK expression, e.g., squamous cell carcinoma, melanoma or leukemia.

In another preferred embodiment the dsRNA silences the JNK gene, and thus can be used to treat a subject having or at risk for a disorder characterized by unwanted JNK expression, e.g., pancreatic or breast cancers.

In a preferred embodiment the dsRNA silences the RAF gene, and thus can be used to treat a subject having or at risk for a disorder characterized by unwanted RAF expression, e.g., lung cancer or leukemia.

In a preferred embodiment the dsRNA silences the Erk1/2 gene, and thus can be used to treat a subject having or at risk for a disorder characterized by unwanted Erk1/2 expression, e.g., lung cancer.

In another preferred embodiment the dsRNA silences the PCNA(p21) gene, and thus can be used to treat a subject having or at risk for a disorder characterized by unwanted PCNA expression, e.g., lung cancer.

In a preferred embodiment the dsRNA silences the MYB gene, and thus can be used to treat a subject having or at risk for a disorder characterized by unwanted MYB expression, e.g., colon cancer or chronic myelogenous leukemia.

In a preferred embodiment the dsRNA silences the c-MYC gene, and thus can be used to treat a subject having or at risk for a disorder characterized by unwanted c-MYC expression, e.g., Burkitt's lymphoma or neuroblastoma.

In another preferred embodiment the dsRNA silences the JUN gene, and thus can be used to treat a subject having or at risk for a disorder characterized by unwanted JUN expression, e.g., ovarian, prostate or breast cancers.

In another preferred embodiment the dsRNA silences the FOS gene, and thus can be used to treat a subject having or at risk for a disorder characterized by unwanted FOS expression, e.g., skin or prostate cancers.

In a preferred embodiment the dsRNA silences the BCL2 gene, and thus can be used to treat a subject having or at risk for a disorder characterized by unwanted BCL-2 expression, e.g., lung or prostate cancers or Non-Hodgkin lymphoma.

In a preferred embodiment the dsRNA silences the Cyclin D gene, and thus can be used to treat a subject having or at risk for a disorder characterized by unwanted Cyclin D expression, e.g., esophageal and colon cancers.

In a preferred embodiment the dsRNA silences the VEGF gene, and thus can be used to treat a subject having or at risk for a disorder characterized by unwanted VEGF expression, e.g., esophageal and colon cancers.

In a preferred embodiment the dsRNA silences the VEGFR1 (Flt-1) gene, and thus can be used to treat a subject having or at risk for a disorder characterized by unwanted VEGFR1 expression, e.g., breast and lung cancer.

In a preferred embodiment the dsRNA silences the VEGFR2 (Flk-1/KDR) gene, and thus can be used to treat a subject having or at risk for a disorder characterized by unwanted VEGFR2 expression, e.g., breast, prostate, and colon cancers.

In a preferred embodiment the dsRNA silences the EGFR gene, and thus can be used to treat a subject having or at risk for a disorder characterized by unwanted EGFR expression, e.g., breast cancer.

In a preferred embodiment the dsRNA silences the EGF gene, and thus can be used to treat a subject having or at risk for a disorder characterized by unwanted EGF expression, e.g., breast and ovarian cancer.

In another preferred embodiment the dsRNA silences the Cyclin A gene, and thus can be used to treat a subject having or at risk for a disorder characterized by unwanted Cyclin A expression, e.g., lung and cervical cancers.

In another preferred embodiment the dsRNA silences the Cyclin E gene, and thus can be used to treat a subject having or at risk for a disorder characterized by unwanted Cyclin E expression, e.g., lung and breast cancers.

In another preferred embodiment the dsRNA silences the WNT-1 gene, and thus can be used to treat a subject having or at risk for a disorder characterized by unwanted WNT-1 expression, e.g., basal cell carcinoma.

In another preferred embodiment the dsRNA silences the beta-catenin gene, and thus can be used to treat a subject having or at risk for a disorder characterized by unwanted beta-catenin expression, e.g., adenocarcinoma or hepatocellular carcinoma.

In another preferred embodiment the dsRNA silences the c-MET gene, and thus can be used to treat a subject having or at risk for a disorder characterized by unwanted c-MET expression, e.g., hepatocellular carcinoma.

In another preferred embodiment the dsRNA silences the PKC gene, and thus can be used to treat a subject having or at risk for a disorder characterized by unwanted PKC expression, e.g., breast cancer.

In a preferred embodiment the dsRNA silences the NFKB gene, and thus can be used to treat a subject having or at risk for a disorder characterized by unwanted NFKB expression, e.g., breast cancer.

In a preferred embodiment the dsRNA silences the STAT3 gene, and thus can be used to treat a subject having or at risk for a disorder characterized by unwanted STAT3 expression, e.g., prostate cancer.

In another preferred embodiment the dsRNA silences the survivin gene, and thus can be used to treat a subject having or at risk for a disorder characterized by unwanted survivin expression, e.g., cervical or pancreatic cancers.

In another preferred embodiment the dsRNA silences the Erb2/Her2/Neu gene, and thus can be used to treat a subject having or at risk for a disorder characterized by unwanted Erb2/Her2/Neu expression, e.g., breast cancer.

In another preferred embodiment the dsRNA silences the topoisomerase I gene, and thus can be used to treat a subject having or at risk for a disorder characterized by unwanted topoisomerase I expression, e.g., ovarian and colon cancers.

In a preferred embodiment the dsRNA silences the topoisomerase II alpha gene, and thus can be used to treat a subject having or at risk for a disorder characterized by unwanted topoisomerase II expression, e.g., breast and colon cancers.

In a preferred embodiment the dsRNA silences mutations in the p73 gene, and thus can be used to treat a subject having or at risk for a disorder characterized by unwanted p73 expression, e.g., colorectal adenocarcinoma.

In a preferred embodiment the dsRNA silences mutations in the p21(WAF1/CIP1) gene, and thus can be used to treat a subject having or at risk for a disorder characterized by unwanted p21(WAF1/CIP1) expression, e.g., liver cancer.

In a preferred embodiment the dsRNA silences mutations in the p27(KIP1) gene, and thus can be used to treat a subject having or at risk for a disorder characterized by unwanted p27(KIP1) expression, e.g., liver cancer.

In a preferred embodiment the dsRNA silences mutations in the PPM1D gene, and thus can be used to treat a subject having or at risk for a disorder characterized by unwanted PPM1D expression, e.g., breast cancer.

In another preferred embodiment the dsRNA silences mutations in the caveolin I gene, and thus can be used to treat a subject having or at risk for a disorder characterized by unwanted caveolin I expression, e.g., esophageal squamous cell carcinoma.

In another preferred embodiment the dsRNA silences mutations in the MIB I gene, and thus can be used to treat a subject having or at risk for a disorder characterized by unwanted MIB I expression, e.g., male breast carcinoma (MBC).

In another preferred embodiment the dsRNA silences mutations in the MTAI gene, and thus can be used to treat a subject having or at risk for a disorder characterized by unwanted MTAI expression, e.g., ovarian carcinoma.

In another preferred embodiment the dsRNA silences mutations in the M68 gene, and thus can be used to treat a subject having or at risk for a disorder characterized by unwanted M68 expression, e.g., human adenocarcinomas of the esophagus, stomach, colon, and rectum.

In another preferred embodiment the dsRNA silences mutations in the cdk2 gene, and thus can be used to treat a subject having or at risk for a disorder characterized by unwanted cdk2 expression, e.g., ovarian carcinoma.

In another preferred embodiment the dsRNA silences mutations in the chk1 gene, and thus can be used to treat a subject having or at risk for a disorder characterized by unwanted chk1 expression, e.g., cancer In another preferred embodiment the dsRNA silences mutations in the chk2 gene, and thus can be used to treat a subject having or at risk for a disorder characterized by unwanted chk2, expression, e.g., cancer.

In another preferred embodiment the dsRNA silences mutations in the plk1 gene, and thus can be used to treat a subject having or at risk for a disorder characterized by unwanted plk1 expression, e.g., cancer.

In another preferred embodiment the dsRNA silences mutations in the Eg5/KSP (KiF11) gene, and thus can be used to treat a subject having or at risk for a disorder characterized by unwanted Eg5/KSP expression, e.g., cancer.

In another preferred embodiment the dsRNA silences mutations in the E-cadherin gene, and thus can be used to treat a subject having or at risk for a disorder characterized by unwanted E-cadherin expression, e.g., cancer.

In another preferred embodiment the dsRNA silences mutations in the akt gene, and thus can be used to treat a subject having or at risk for a disorder characterized by unwanted akt expression, e.g., cancer.

In another preferred embodiment the dsRNA silences mutations in the p85a (map kinase activated protein kinase) gene, and thus can be used to treat a subject having or at risk for a disorder characterized by unwanted p85a expression, e.g., cancer.

In another preferred embodiment the dsRNA silences mutations in the Bcl-XL gene, and thus can be used to treat a subject having or at risk for a disorder characterized by unwanted Bcl-XL expression, e.g., cancer.

In another preferred embodiment the dsRNA silences mutations in the SMAD7 gene, and thus can be used to treat a subject having or at risk for a disorder characterized by unwanted SMAD7 expression, e.g., cancer.

In another preferred embodiment the dsRNA silences mutations in the HIF1 gene, and thus can be used to treat a subject having or at risk for a disorder characterized by unwanted HIF1 expression, e.g., cancer.

In another preferred embodiment the dsRNA silences mutations in the MMP1 (matrix metalloprotease 1) gene, and thus can be used to treat a subject having or at risk for a disorder characterized by unwanted MMP1 expression, e.g., breast and colorectal cancer.

In another preferred embodiment the dsRNA silences mutations in the MMP2 (matrix metalloprotease 2) gene, and thus can be used to treat a subject having or at risk for a disorder characterized by unwanted MMP2 expression, e.g., breast, ovarian, pancreatic and colon cancer.

In another preferred embodiment the dsRNA silences mutations in the MMP9 (matrix metalloprotease 9) gene, and thus can be used to treat a subject having or at risk for a disorder characterized by unwanted MMP9 expression, e.g., breast, ovarian, pancreatic and colon cancer.

In another preferred embodiment the dsRNA silences mutations in the HDAC (histone deacetylase) gene (i.e., histone deacetylase genes 1-6 and 9), and thus can be used to treat a subject having or at risk for a disorder characterized by unwanted HDAC expression, e.g., cancer.

In another preferred embodiment the dsRNA silences mutations in the TERT (telomerase reverse transcriptase) gene, and thus can be used to treat a subject having or at risk for a disorder characterized by unwanted TERT expression, e.g., cancer.

In another preferred embodiment the dsRNA silences mutations in the Aurora A gene, and thus can be used to treat a subject having or at risk for a disorder characterized by unwanted Aurora A expression, e.g., cancer.

In another preferred embodiment the dsRNA silences mutations in the Aurora B gene, and thus can be used to treat a subject having or at risk for a disorder characterized by unwanted Aurora B expression, e.g., cancer.

In another preferred embodiment the dsRNA silences mutations in the thymidylate synthase gene, and thus can be used to treat a subject having or at risk for a disorder characterized by unwanted thymidylate synthase expression, e.g., cancer.

In preferred embodiments the dsRNA silences mutations in tumor suppressor genes, and thus can be used as a method to promote apoptotic activity in combination with chemo-therapeutics.

In a preferred embodiment the dsRNA silences mutations in the p53 tumor suppressor gene, and thus can be used to treat a subject having or at risk for a disorder characterized by unwanted p53 expression, e.g., gall bladder, pancreatic and lung cancers.

In a preferred embodiment the dsRNA silences mutations in the p53 family member DN-p63, and thus can be used to treat a subject having or at risk for a disorder characterized by unwanted DN-p63 expression, e.g., squamous cell carcinoma.

In a preferred embodiment the dsRNA silences mutations in the pRb tumor suppressor gene, and thus can be used to treat a subject having or at risk for a disorder characterized by unwanted pRb expression, e.g., oral squamous cell carcinoma.

In a preferred embodiment the dsRNA silences mutations in the APC1 tumor suppressor gene, and thus can be used to treat a subject having or at risk for a disorder characterized by unwanted APC1 expression, e.g., colon cancer.

In a preferred embodiment the dsRNA silences mutations in the BRCA1 tumor suppressor gene, and thus can be used to treat a subject having or at risk for a disorder characterized by unwanted BRCA1 expression, e.g., breast cancer.

In a preferred embodiment the dsRNA silences mutations in the PTEN tumor suppressor gene, and thus can be used to treat a subject having or at risk for a disorder characterized by unwanted PTEN expression, e.g., hamartomas, gliomas, and prostate and endometrial cancers.

In a preferred embodiment the dsRNA silences MLL fusion genes, e.g. MLL-AF9, and thus can be used to treat a subject having or at risk for a disorder characterized by unwanted MLL fusion gene expression, e.g., acute leukemias.

In another preferred embodiment the dsRNA silences the BCR/ABL fusion gene, and thus can be used to treat a subject having or at risk for a disorder characterized by unwanted BCR/ABL fusion gene expression, e.g., acute and chronic leukemias.

In another preferred embodiment the dsRNA silences the TEL/AML1 fusion gene, and thus can be used to treat a subject having or at risk for a disorder characterized by unwanted TEL/AML1 fusion gene expression, e.g., childhood acute leukemia.

In another preferred embodiment the dsRNA silences the EWS/FLI1 fusion gene, and thus can be used to treat a subject having or at risk for a disorder characterized by unwanted EWS/FLI1 fusion gene expression, e.g., Ewing Sarcoma.

In another preferred embodiment the dsRNA silences the TLS/FUS1 fusion gene, and thus can be used to treat a subject having or at risk for a disorder characterized by unwanted TLS/FUS1 fusion gene expression, e.g., Myxoid liposarcoma.

In another preferred embodiment the dsRNA silences the PAX3/FKHR fusion gene, and thus can be used to treat a subject having or at risk for a disorder characterized by unwanted PAX3/FKHR fusion gene expression, e.g., Myxoid liposarcoma.

In another preferred embodiment the dsRNA silences the AML1/ETO fusion gene, and thus can be used to treat a subject having or at risk for a disorder characterized by unwanted AML1/ETO fusion gene expression, e.g., acute leukemia.

Another aspect of the invention relates to a method of treating a subject, e.g., a human, at risk for or afflicted with a disease or disorder that may benefit by angiogenesis inhibition e.g., cancer. The method comprises providing a dsRNA, wherein the dsRNA can inhibit by RNA interference, a gene which mediates angiogenesis; and administering a therapeutically effective dosage of said dsRNA to a subject, preferably a human.

In a preferred embodiment the dsRNA silences the alpha v-integrin gene, and thus can be used to treat a subject having or at risk for a disorder characterized by unwanted alpha V integrin, e.g., brain tumors or tumors of epithelial origin.

In a preferred embodiment the dsRNA silences the Flt-1 receptor gene, and thus can be used to treat a subject having or at risk for a disorder characterized by unwanted Flt-1 receptors, eg. Cancer and rheumatoid arthritis.

In a preferred embodiment the dsRNA silences the tubulin gene, and thus can be used to treat a subject having or at risk for a disorder characterized by unwanted tubulin, eg. Cancer and retinal neovascularization.

The pharmaceutical compositions of the present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

Another aspect of the invention relates to a method of treating a subject, e.g., a human, at risk for or afflicted with a disease or disorder characterized by an unwanted immune response, e.g., an inflammatory disease or disorder, or an autoimmune disease or disorder. The method comprises providing a dsRNA, wherein said dsRNA can inhibit by RNA interference, a gene which mediates an unwanted immune response; and administering said dsRNA to a subject, preferrably a human subject. In a preferred embodiment the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplantated organ or tissue, e.g., transplanted cardiac or vascular tissue; or thrombolysis. In a preferred embodiment the disease or disorder is restenosis, e.g., restenosis associated with surgical intervention e.g., angioplasty, e.g., percutaneous transluminal coronary angioplasty. In a preferred embodiment the disease or disorder is Inflammatory Bowel Disease, e.g., Crohn Disease or Ulcerative Colitis. In a preferred embodiment the disease or disorder is inflammation associated with an infection or injury. In a preferred embodiment the disease or disorder is asthma, lupus, multiple sclerosis, diabetes, e.g., type II diabetes, arthritis, e.g., rheumatoid or psoriatic. In particularly preferred embodiments the dsRNA silences an integrin or co-ligand thereof, e.g., VLA4, VCAM, ICAM. In particularly preferred embodiments the dsRNA silences a selectin or co-ligand thereof, e.g., P-selectin, E-selectin (ELAM), I-selectin, P-selectin glycoprotein-1 (PSGL-1). In particularly preferred embodiments the dsRNA silences a component of the complement system, e.g., C3, C5, C3aR, C5aR, C3 convertase, C5 convertase.

In particularly preferred embodiments the dsRNA silences a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, CCR3, and CCR2.

In other embodiments the dsRNA silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, and I-309.

In still other embodiments the dsRNA silences Bax, CD40, CD40L, MyD88, NF-kappa-B, IKK1 (inhibitor of NF-kappa-B1), IKK2 (inhibitor of NF-kappa-B1), IRAK1, IRAK2, IRAK3, IRAK4, PU.1 (spleen focus forming virus proviral integration oncogene), adenosine A2 receptor, STAT1, p38 (map kinase mitogen activated protein kinase) and CTLA4.

Another aspect of the invention features a method of treating a subject, e.g., a human, at risk for or afflicted with acute pain or chronic pain. The method comprises providing a dsRNA, wherein said dsRNA can inhibit by RNA interference, a gene which mediates the processing of pain; and administering a therapeutically effective dose of said dsRNA to a subject, preferrably a human subject. In particularly preferred embodiments the dsRNA silences a component of an ion channel. In particularly preferred embodiments the dsRNA silences a neurotransmitter receptor or ligand.

Another aspect of the invention relates to a method of treating a subject, e.g., a human, at risk for or afflicted with a neurological disease or disorder. The method comprises providing a dsRNA, wherein said dsRNA can inhibit by RNA interference, a gene which mediates a neurological disease or disorder; and administering a therapeutically effective dose of said dsRNA to a subject, preferably a human. In a preferred embodiment the disease or disorder is Alzheimer Disease or Parkinson Disease. In particularly preferred embodiments the dsRNA silences an amyloid-family gene, e.g., APP; a presenilin gene, e.g., PSEN1 and PSEN2, or I-synuclein. In a preferred embodiment the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In particularly preferred embodiments the dsRNA silences huntingtin (HD), DRPLA, SCA1, SCA2, MJD1, CACNL1A4, SCA7, SCA8, alpha-synuclein, beta-amyloid converting enzyme, amyloid beta precursor protein (APP), caspase-3, vanilloid receptor (VR), Scn-1A/NAV1.8 (sodium channel voltage gated type X alpha protein), Scn-2A/NAV1.2 (sodium channel voltage gated type X alpha protein), KCNN3, Parkin, and Tau.

In another embodiment, the invention relates to a method for treating viral diseases, including but not limited to hepatitis C, hepatitis B, hepatitis A, herpes simplex virus (HSV), human papilloma virus (HPV), HIV-AIDS, poliovirus, and smallpox virus. dsRNA of the invention are prepared as described herein to target expressed sequences of a virus, thus ameliorating viral activity and replication. The dsRNA can be used in the treatment and/or diagnosis of viral infected tissue, both animal and plant. Also, such dsRNA can be used in the treatment of virus-associated carcinoma, such as hepatocellular cancer.

For example, the dsRNA of the present invention are useful for treating a subject having an infection or a disease associated with the replication or activity of a (+) strand RNA virus having a 3'-UTR, such as HCV. In this embodiment, the dsRNA can act as novel therapeutic agents for inhibiting replication of the virus. The method comprises administering a pharmaceutical composition of the invention to the patient (e.g., human), such that viral replication is inhibited. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of aliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus). In a preferred embodiment, the virus is hepacivirus, the hepatitis C virus. Although the foregoing list exemplifies vertebrate viruses, the present invention encompasses the compositions and methods for treating infections and diseases caused by any (+) strand RNA virus having a 3'-UTR, regardless of the host. For example, the invention encompasses the treatment of plant diseases caused by sequiviruses, comoviruses, potyviruses, sobemovirus, luteoviruses, tombusviruses, tobavirus, tobravirus, bromoviruses, and closteroviruses.

Another aspect of the invention relates to a method of treating a subject infected with a virus or at risk for or afflicted with a disorder or disease associated with a viral infection. The method comprises providing a dsRNA, wherein the dsRNA can inhibit by RNA interference, a viral gene of a cellular gene which mediates viral function, e.g., entry or growth; and administering a therapeutically effective dose of said dsRNA to a subject, preferably a human subject.

Thus, the invention provides for a method of treating patients infected by the Human Papilloma Virus (HPV) or at risk for or afflicted with a disorder mediated by HPV, e.g, cervical cancer. HPV is linked to 95% of cervical carcinomas and thus an antiviral therapy is an attractive method to treat these cancers and other symptoms of viral infection.

In a preferred embodiment, the expression of a HPV gene is reduced. In another preferred embodiment, the HPV gene is one of the group of E2, E6, or E7.

In a preferred embodiment the expression of a human gene that is required for HPV replication is reduced.

The invention a Iso includes a method of treating patients infected by the Human Immunodeficiency Virus (HIV) or at risk for or afflicted with a disorder mediated by HIV, e.g., Acquired Immune Deficiency Syndrome (AIDS). In a preferred embodiment, the expression of a HIV gene is reduced. In another preferred embodiment, the HIV gene is CCR5, Gag, or Rev. In a preferred embodiment the expression of a human gene that is required for HIV replication is reduced. In another preferred embodiment, the gene is CD4 or Tsg101.

The invention also includes a method for treating patients infected by the Hepatitis B Virus (HBV) or at risk for or afflicted with a disorder mediated by HBV, e.g., cirrhosis and heptocellular carcinoma. In a preferred embodiment, the expression of a HBV gene is reduced. In another preferred embodiment, the targeted HBV gene encodes one of the group of the tail region of the HBV core protein, the precregious (pre-c) region, or the cregious (c) region. In another preferred embodiment, a targeted HBV-RNA sequence is comprised of the poly(A) tail.

In preferred embodiment the expression of a human gene that is required for HBV replication is reduced.

The invention also provides for a method of treating patients infected by the Hepatitis A Virus (HAV), or at risk for or afflicted with a disorder mediated by HAV. In a preferred embodiment the expression of a human gene that is required for HAV replication is reduced.

The present invention provides for a method of treating patients infected by the Hepatitis C Virus (HCV), or at risk for or afflicted with a disorder mediated by HCV, e.g., cirrhosis. In a preferred embodiment, the expression of a HCV gene is reduced. In another preferred embodiment the expression of a human gene that is required for HCV replication is reduced.

The present invention also provides for a method of treating patients infected by the any of the group of Hepatitis Viral strains comprising hepatitis D, E, F, G, or H, or patients at risk for or afflicted with a disorder mediated by any of these strains of hepatitis. In a preferred embodiment, the expression of a Hepatitis, D, E, F, G, or H gene is reduced. In another preferred embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g, lower respiratory tract infection in infants and childhood asthma, pneumonia and other complications, e.g., in the elderly. In a preferred embodiment, the expression of a RSV gene is reduced. In another preferred embodiment, the targeted HBV gene encodes one of the group of genes N, L, or P. In a preferred embodiment the expression of a human gene that is required for RSV replication is reduced.

Methods of the invention provide for treating patients infected by the Herpes Simplex Virus (HSV) or at risk for or afflicted with a disorder mediated by HSV, e.g, genital herpes and cold sores as well as life-threatening or sight-impairing disease mainly in immunocompromised patients. In a preferred embodiment, the expression of a HSV gene is reduced. In another preferred embodiment, the targeted HSV gene encodes DNA polymerase or the helicase-primase. In a preferred embodiment the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients. In a preferred embodiment, the expression of a CMV gene is reduced. In a preferred embodiment the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease. In a preferred embodiment, the expression of a EBV gene is reduced. In a preferred embodiment the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma. In a preferred embodiment, the expression of a KSHV gene is reduced. In a preferred embodiment the expression of a human gene that is required for KSHV replication is reduced.

The invention also includes a method for treating patients infected by the JC Virus (JCV) or a disease or disorder associated with this virus, e.g., progressive multifocal leukoencephalopathy (PML). In a preferred embodiment, the expression of a JCV gene is reduced. In preferred embodiment the expression of a human gene that is required for JCV replication is reduced.

Methods of the invention also provide for treating patients infected by Severe Acute Respiratory Syndrome (SARS) or at risk for or afflicted with a disorder mediated by SARS as well as life-threatening or sight-impairing disease mainly in immunocompromised patients. In a preferred embodiment, the expression of a SARS gene is reduced.

Methods of the invention also provide for treating patients infected by the myxovirus or at risk for or afflicted with a disorder mediated by myxovirus, e.g., influenza. In a preferred embodiment, the expression of a myxovirus gene is reduced. In a preferred embodiment the expression of a human gene that is required for myxovirus replication is reduced.

Methods of the invention also provide for treating patients infected by the rhinovirus or at risk for of afflicted with a disorder mediated by rhinovirus, e.g., the common cold. In a preferred embodiment, the expression of a rhinovirus gene is reduced. In preferred embodiment the expression of a human gene that is required for rhinovirus replication is reduced.

Methods of the invention also provide for treating patients infected by the coronavirus or at risk for of afflicted with a disorder mediated by coronavirus, e.g., the common cold. In a preferred embodiment, the expression of a coronavirus gene is reduced. In preferred embodiment the expression of a human gene that is required for coronavirus replication is reduced.

Methods of the invention also provide for treating patients infected by the flavivirus West Nile or at risk for or afflicted with a disorder mediated by West Nile Virus. In a preferred embodiment, the expression of a West Nile Virus gene is reduced. In another preferred embodiment, the West Nile Virus gene is one of the group comprising E, NS3, or NS5. In a preferred embodiment the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral haemorrhagic fever or neurological disease. In a preferred embodiment, the expression of a St. Louis Encephalitis gene is reduced. In a preferred embodiment the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral haemorrhagic fever and neurological disease. In a preferred embodiment, the expression of a Tick-borne encephalitis virus gene is reduced. In a preferred embodiment the expression of a human gene that is required for Tick-borne encephalitis virus replication is reduced.

Methods of the invention also provide for methods of treating patients infected by the Murray Valley encephalitis flavivirus, which commonly results in viral haemorrhagic fever and neurological disease. In a preferred embodiment, the expression of a Murray Valley encephalitis virus gene is reduced. In a preferred embodiment the expression of a human gene that is required for Murray Valley encephalitis virus replication is reduced.

The invention also includes methods for treating patients infected by the dengue flavivirus, or a disease or disorder associated with this virus, e.g., dengue haemorrhagic fever. In a preferred embodiment, the expression of a dengue virus gene is reduced. In a preferred embodiment the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis. In a preferred embodiment, the expression of a SV40 gene is reduced. In a preferred embodiment the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy. In a preferred embodiment, the expression of a HTLV gene is reduced. In another preferred embodiment the HTLV1 gene is the Tax transcriptional activator. In a preferred embodiment the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia. In a preferred embodiment, the expression of a Mo-MuLV gene is reduced. In a preferred embodiment the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g. myocarditis. EMCV leads to myocarditis in mice and pigs and is capable of infecting human myocardial cells. This virus is therefore a concern for patients undergoing xenotransplantation. In a preferred embodiment, the expression of a EMCV gene is reduced. In a preferred embodiment the expression of a human gene that is required for EMCV replication is reduced.

The invention also includes a method for treating patients infected by the measles virus (MV) or at risk for or afflicted with a disorder mediated by MV, e.g., measles. In a preferred embodiment, the expression of a MV gene is reduced. In a preferred embodiment the expression of a human gene that is required for MV replication is reduced.

The invention also includes a method for treating patients infected by the Varicella zoster virus (VZV) or at risk for or afflicted with a disorder mediated by VZV, e.g. chicken pox or shingles (also called zoster). In a preferred embodiment, the expression of a VZV gene is reduced. In a preferred embodiment the expression of a human gene that is required for VZV replication is reduced.

The invention also includes a method for treating patients infected by an adenovirus or at risk for or afflicted with a disorder mediated by an adenovirus, e.g. respiratory tract infection. In a preferred embodiment, the expression of an adenovirus gene is reduced. In a preferred embodiment the expression of a human gene that is required for adenovirus replication is reduced.

The invention includes a method for treating patients infected by a yellow fever virus (YFV) or at risk for or afflicted with a disorder mediated by a YFV, e.g. respiratory tract infection. In a preferred embodiment, the expression of a YFV gene is reduced. In another preferred embodiment, the preferred gene is one of a group that includes the E, NS2A, or NS3 genes. In a preferred embodiment the expression of a human gene that is required for YFV replication is reduced.

Methods of the invention also provide for treating patients infected by the poliovirus or at risk for or afflicted with a disorder mediated by poliovirus, e.g., polio. In a preferred embodiment, the expression of a poliovirus gene is reduced. In a preferred embodiment the expression of a human gene that is required for poliovirus replication is reduced.

Methods of the invention also provide for treating patients infected by a poxvirus or at risk for or afflicted with a disorder mediated by a poxvirus, e.g., smallpox. In a preferred embodiment, the expression of a poxvirus gene is reduced. In a preferred embodiment the expression of a human gene that is required for poxvirus replication is reduced.

In another, aspect the invention features methods of treating a subject infected with a pathogen, e.g., a bacterial, amoebic, parasitic, or fungal pathogen. The method comprises providing an dsRNA, wherein said dsRNA can inhibit by RNA interference, a pathogen gene; and administering a therapeutically effective dose of said dsRNA to a subject, preferably a human subject.

The target gene can be one involved in growth, cell wall synthesis, protein synthesis, transcription, energy metabolism, e.g., the Krebs cycle, or toxin production. Thus, the present invention provides for a method of treating patients infected by a *plasmodium* that causes malaria. In a preferred embodiment, the expression of a *plasmodium* gene is reduced. In another preferred embodiment, the gene is apical membrane antigen 1 (AMA1). In a preferred embodiment the expression of a human gene that is required for *plasmodium* replication is reduced.

The invention also includes methods for treating patients infected by the *Mycobacterium ulcerans*, or a disease or disorder associated with this pathogen, e.g. Buruli ulcers. In a preferred embodiment, the expression of a *Mycobacterium ulcerans* gene is reduced. In a preferred embodiment the expression of a human gene that is required for *Mycobacterium ulcerans* replication is reduced.

The invention also includes methods for treating patients infected by the *Mycobacterium tuberculosis*, or a disease or disorder associated with this pathogen, e.g. tuberculosis. In a preferred embodiment, the expression of a *Mycobacterium tuberculosis* gene is reduced. In a preferred embodiment the expression of a human gene that is required for *Mycobacterium tuberculosis* replication is reduced.

The invention also includes methods for treating patients infected by the *Mycobacterium leprae*, or a disease or disorder associated with this pathogen, e.g. leprosy. In a preferred embodiment, the expression of a *Mycobacterium leprae* gene is reduced. In a preferred embodiment the expression of a human gene that is required for *Mycobacterium leprae* replication is reduced.

The invention also includes methods for treating patients infected by the bacteria *Staphylococcus aureus*, or a disease or disorder associated with this pathogen, e.g. infections of the skin and muscous membranes. In a preferred embodiment, the expression of a *Staphylococcus aureus* gene is reduced. In a preferred embodiment the expression of a human gene that is required for *Staphylococcus aureus* replication is reduced.

The invention also includes methods for treating patients infected by the bacteria *Streptococcus pneumoniae*, or a disease or disorder associated with this pathogen, e.g. pneumonia or childhood lower respiratory tract infection. In a preferred embodiment, the expression of a *Streptococcus pneumoniae* gene is reduced. In a preferred embodiment the expression of a human gene that is required for *Streptococcus pneumoniae* replication is reduced.

The invention also includes methods for treating patients infected by the bacteria *Streptococcus pyogenes*, or a disease or disorder associated with this pathogen, e.g. Strep throat or Scarlet fever. In a preferred embodiment, the expression of a *Streptococcus pyogenes* gene is reduced. In a preferred embodiment the expression of a human gene that is required for *Streptococcus pyogenes* replication is reduced.

The invention also includes methods for treating patients infected by the bacteria *Chlamydia pneumoniae*, or a disease or disorder associated with this pathogen, e.g. pneumonia or childhood lower respiratory tract infection. In a preferred embodiment, the expression of a *Chlamydia pneumoniae* gene is reduced. In a preferred embodiment the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g. pneumonia or childhood lower respiratory tract infection. In a preferred embodiment, the expression of a *Mycoplasma pneumoniae* gene is reduced. In a preferred embodiment the expression of a human gene that is required for *Mycoplasma pneumoniae* replication is reduced.

The pharmaceutical compositions of the present invention can also be used to treat a variety of metabolic disorders, in particular those associated with overexpression of a gene or expression of a mutant gene. Example of metabolic disorders or diseases include without limitation, carbohydrate metabolism disorders (including diabetes mellitus, diabetic ketoacidosis, alcoholic ketoacidosis, nonketotic hyperglyemic-hyperosmolar coma, and hypoglycemia), pituitary disorders, thyroid disorders (including hyperthyroidism, hypothyroidism, euthyroid goiter, euthyroid sick syndrome, thyroiditis, and thyroid cancers), adrenal disorders (including adrenal cortical hypofunction, adrenal cortical hyperfunction, pheochromocytoma, and non-functional adrenal masses), multiple endocrine neoplasia syndromes, polyglandular deficiency syndromes, porphyrias (i.e., disorders caused by deficiencies of enzymes of the heme biosynthetic pathway), hyperlipidemia, lipidoses, carcinoid tumors, amyloidosis, obesity, and disorders related to water, electrolyte, mineral, and acid-base metabolism.

Another aspect of the invention relates to a method of treating a subject, e.g., a human, at risk for or afflicted with a metabolic disease or disorder. The method comprises providing a dsRNA, wherein said dsRNA can inhibit by RNA interference, a gene which mediates a metabolic disease or disorder; and administering a therapeutically effective dose of said dsRNA to a subject, preferably a human. In a preferred embodiment the disease or disorder is diabetes mellitus or obesity. In particularly preferred embodiments the dsRNA silences PTP-1B, glucose-6-phosphatase, PEPCK, FoxO-1, FoxA-3, Fructose-1,6-biphosphatase, SREBP1C, SCAP, ApoB, SERBP-2, LDLR, Dhcr24, HMG Co-reductase, FAS-fatty acid synthase, caspase 8, TGF-beta 1, TGF-beta 1 receptor 1, collagen, stearoyl-CoA desaturase 1, microsomal trigylceride transfer protein, dipeptidylpeptidase IV, acetyl-CoA-carboxylase-2,11-hydroxysteroid dehydrogenase 1, APS (adaptor protein with pleckstrin homology and src homology 2 domains), GM3 synthase, acyl CoA:DAG acyltransferase 1, resistin, SHIP-2, hormone sensitive lipase, and PCSK-9.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with a dsRNA of the invention. The dsRNA is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH. E.g., one of ordinary skill in the art can identify essential genes which are in proximity to tumor suppressor genes, and which are within a LOH region which includes the tumor suppressor gene. The gene encoding the large subunit of human RNA polymerase II, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-1 subunit, and transferrin receptor.

Accordingly, another aspect of the invention relates to a method of treating a disorder characterized by LOH, e.g., cancer. The method comprises optionally, determining the genotype of the allele of a gene in the region of LOH and preferably determining the genotype of both alleles of the gene in a normal cell; providing a dsRNA, wherein said dsRNA can inhibit by RNA interference, the allele found in the LOH cells; and administering a therapeutically effective dose of said dsRNA to the subject, preferably a human.

The invention also includes a dsRNA disclosed herein, e.g, an dsRNA which can preferentially silences, one allele of a polymorphic gene.

In another aspect, the invention provides a method of cleaving or silencing more than one gene with a dsRNA. In these embodiments the dsRNA is selected so that it has sufficient homology to a sequence found in more than one gene. For example, the sequence AAGCTGGCCCTGGACATG-GAGAT (SEQ ID NO: 43) is conserved between mouse lamin B1, lamin B2, keratin complex 2-gene 1 and lamin A/C. Thus a dsRNA targeted to this sequence would effectively silence the entire collection of genes.

The invention also includes a dsRNA disclosed herein, which can silence more than one gene.

The pharmaceutical compositions encompassed by the invention may be administered by any means known in the art including, but not limited to, oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

VI. Methods for Inhibiting Expression of a Target Gene

In yet another aspect, the invention relates to a method for inhibiting the expression of a target gene in a cell or organism. In one embodiment, the method comprises administering the inventive dsRNA or a pharmaceutical composition comprising the dsRNA to an organism, such as a mammal, such that expression of the target gene is silenced. Because of their surprisingly improved stability and bioavailability, the dsRNA of the present invention effectively inhibit expression or activity of target genes at surprisingly low dosages. Compositions and methods for inhibiting the expression of a target gene using dsRNA can be performed as described in the preceding sections, particularly Sections IV and V, which are hereby incorporated by reference.

In this embodiment, a pharmaceutical composition comprising the dsRNA may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

The methods for inhibiting the expression of a target gene can be applied to any mammalian gene one wishes to silence, thereby specifically inhibiting its expression. Examples of genes which can be targeted for silencing include, without limitation, developmental genes including but not limited to adhesion molecules, cyclin kinase inhibitors, Wnt family members, Pax family members, Winged helix family members, Hox family members, cytokines/Lymphokines and their receptors, growth/differentiation factors and their receptors, and neurotransmitters and their receptors; (2) oncogenes including but not limited to ABLI, BCL1, BCL2, BCL6, CBFA2, CBL, CSFIR, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES; (3) tumor suppressor genes including but not limited APC, BRCA1, BRCA2, MADH4, MCC, NF1, NF2, RB1, TP53 and WT1; (4) enzymes including but not limited to ACP desaturases and hydroxylases, ADP-glucose pyrophorylases, ATPases, alcohol dehydrogenases, amylases, amyloglucosidases, catalases, cellulases, cyclooxygenases, decarboxylases, dextrinases, DNA and RNA polymerases, galactosidases, glucanases, glucose oxidases, GTPases, helicases, hemicellulases, integrases, invertases, isomerases, kinases, lactases, lipases, lipoxygenases, lysozymes, pectinesterases, peroxidases, phosphatases, phospholipases, phosphorylases, polygalacturonases, proteinases and peptideases, pullanases, recombinases, reverse transcriptases, topoisomerases, and xylanases, and (5) any one of the genes listed in Section V above not yet named under (1) to (4) of this paragraph.

In addition to in vivo gene inhibition, the skilled artisan will appreciate that the dsRNA of the present invention are useful in a wide variety of in vitro applications. Such in vitro applications, include, for example, scientific and commercial research (e.g., elucidation of physiological pathways, drug discovery and development), and medical and veterinary diagnostics. In general, the method involves the introduction of the dsRNA into a cell using known techniques (e.g., absorption through cellular processes, or by auxiliary agents or devices, such as electroporation and lipofection), then maintaining the cell for a time sufficient to obtain degradation of an mRNA transcript of the target gene.

VII. Methods for Identifying dsRNA having Increased Stability

In yet another aspect, the invention relates to methods for identifying dsRNA having increased stability in biological tissues and fluids such as serum. dsRNA having increased stability have enhanced resistance to degradation, e.g., by chemicals or nucleases (exonucleases and endonucleases) which normally degrade RNA molecules. Methods for detecting increases in nucleic acid stability are well known in the art. Any assay capable of measuring or detecting differences between a test dsRNA and a control dsRNA (i.e., a dsRNA that is structurally similar or identical to the test (modified) dsRNA molecule except that is lacks at least one of the substituted or modified nucleotides present in the test dsRNA) in any measurable physical parameter may be suitable for use in the methods of the present invention. In general, because the inhibitory effect of a dsRNA on a target gene activity or expression requires that the molecule remain intact, the stability of a particular dsRNA can be evaluated indirectly by observing or measuring a property associated with the expression of the gene. Thus, the relative stability of a dsRNA can be determined by observing or detecting (1) an absence or observable decrease in the level of the protein encoded by the target gene, (2) an absence or observable decrease in the level of mRNA product from the target gene, and (3) a change or loss in phenotype associated with expression of the target gene. In the context of a medical treatment, the stability of a dsRNA may be evaluated based on the degree of the inhibition of expression or function of the target gene, which in turn may be assessed based on a change in the disease condition of the patient, such as reduction in symptoms, remission, or a change in disease state.

In one embodiment, the method comprises preparing a dsRNA as described in Section III above (e.g., through chemical synthesis), incubating the dsRNA with a biological sample, then analyzing and identifying those dsRNA that exhibit an increased stability as compared to a control dsRNA.

In an exemplary embodiment, dsRNA is produced in vitro by mixing/annealing complementary single-stranded RNA strands, preferably in a molar ratio of at least about 3:7, more preferably in a molar ratio of about 4:6, and most preferably in essentially equal molar amounts (i.e., a molar ratio of about 5:5). Preferably, the single-stranded RNA strands are denatured prior to mixing/annealing, and the buffer in which the mixing/annealing reaction takes place contains a salt, preferably potassium chloride. Single-stranded RNA strands may be synthesized by solid phase synthesis using, for example, an Expedite 8909 synthesizer (Applied Biosystems, Applera Deutschland GmbH, Darmstadt, Germany), as described above.

dsRNA are incubated with a biological sample under the conditions sufficient or optimal for enzymatic function. After incubating with a biological sample, the stability of the dsRNA is analyzed by means conventional in the art, for example using RNA gel electrophoresis as exemplified herein. For example, when the sample is serum, the dsRNA may be incubated at a concentration of 1-10 µM, preferably 2-8 µM, more preferably 3-6 µM, and most preferably 4-5 µM. The incubation temperature is preferably between 25° C. and 45° C., more preferably between 35° C. and 40° C., and most preferably about 37° C.

The biological sample used in the incubation step may be derived from tissues, cells, biological fluids or isolates thereof. For example, the biological sample may be isolated from a subject, such as a whole organism or a subset of its tissues or cells. The biological sample may also be a component part of the subject, such as a body fluid, including but not limited to blood, serum, mucus, lymphatic fluid, synovial fluid, cerebrospinal fluid, saliva, amniotic fluid, amniotic cord blood, urine, vaginal fluid and semen. Preferably, the biological sample is a serum derived from a blood sample of a subject. The subject is preferably a mammal, more preferably a human.

In another embodiment, the method comprises selecting a dsRNA having increased stability by measuring the protein expression levels of a target gene in a cell following introduction of the dsRNA. In this embodiment, the dsRNA of the invention inhibit expression of a target gene in cell, and thus the method comprises selecting a dsRNA that induces a measurable reduction in expression of a target gene as compared to a control dsRNA. Assays that measure the expression levels of proteins can be performed approximately 24 hours following uptake of the dsRNA by the cell (e.g., using Northern blot techniques, RNAe Protection Assays, or QC-PCR assays as known in the art). Preferably, in addition to testing the protein levels of a target gene at regular time intervals following absorption of the test dsRNA, the protein levels of the target gene are also measured at the same time points following absorption of a control dsRNA. The protein levels of the test sample and the control sample are then compared. The test dsRNA is selected as having increased stability when there is a measurable reduction in expression levels as compared to the control dsRNA. Protein measurements can be made using any art-recognized technique (see, e.g., Chiang, M. Y., et al., *J. Biol Chem*. (1991) 266:18162-71; and Fisher, T, et al., *Nucl. Acids Res*. (1993) 21:3857).

The ability of a dsRNA composition of the invention to inhibit protein synthesis can be measured using a variety of techniques that are known in the art. For example, Northern blot analysis can be used to measure the presence of RNA encoding a target protein. The level of the specific mRNA produced by the target protein can be measured, e.g., using PCR. Because dsRNA directs the sequence-specific degradation of endogenous mRNA through RNAi, the selection methods of the invention encompass any technique that is capable of detecting a measurable reduction in the target RNA. In yet another example, Western blots can be used to measure the amount of target protein present. In still another embodiment, a phenotype influenced by the amount of the protein can be detected. Techniques for performing Western blots are well known in the art (see, e.g., Chen, et al., *J. Biol. Chem*. 271:28259).

A portion of the target gene may be fused with a reporter gene so that the reporter gene is transcribed. By monitoring a change in the expression of the reporter gene in the presence of the dsRNA, it is possible to determine the effectiveness of the dsRNA in inhibiting the expression of the reporter gene. The expression levels of the reporter gene in the presence of the test dsRNA versus a control dsRNA are then compared. The test dsRNA is selected as having increased stability when there is a measurable reduction in expression levels of the reporter gene as compared to the control dsRNA. Examples of reporter genes useful for use in the present invention include, without limitation, those coding for luciferase, chloramphenicol acetyl transferase (CAT), β-galactosidase, and alkaline phosphatase. Suitable reporter genes are described, for example, in *Current Protocols in Molecular Biology*, John Wiley & Sons, New York (Ausubel, F. A., et al., eds., 1989); Gould, S. J., and S. Subramani, *Anal. Biochem*. (1988) 7:404-408; Gorman, C. M., et al., *Mol. Cell. Biol*. (1982) 2:1044-1051; and Selden, R., et al., *Mol. Cell. Biol*. (1986) 6:3173-3179; each of which is hereby incorporated by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXEMPLIFICATION

The invention now being generally described, it will be more readily understood by reference to the following examples, which are included merely for purposes of illustration of certain aspects and embodiments of the present invention, and are not intended to limit the invention.

Example 1

RNA Synthesis

Single-stranded RNAs were produced by solid phase synthesis using an Expedite 8909 synthesizer (Applied Biosystems, Applera Deutschland GmbH, Frankfurter Str. 129b, 64293 Darmstadt, Germany). Other standard ribonucleoside phosphoramidites and nucleosides immobilized on CPG (controlled pore glass), a porous support material, were obtained from ChemGenes Corp. (Ashland Technology Center, 200 Horner Ave., Ashland, Mass. 01721), or from Proliga Biochemie GmbH (Georg Hyken Str. 14, Hamburg, Germany). Other synthesis reagents were obtained from the Mallinckrodt Baker Co. (Im Leuschnerpark 4, 64347 Griesheim, Germany). Raw synthesis products were purified with HPLC (System Gold, Beckman Coulter GmbH, 85702 Unterschleissheim, Germany) using an anion exchange column (DNAPac PA 100, Dionex GmbH, Am Wörtzgarten 10, 65510 Idstein). The achieved yield was determined by means of UV light absorption at 260 nm.

The RNAs used in the study were produced by heating equimolar quantities of single-stranded sense- and antisense RNAs in annealing buffer (100 mM NaCl, 20 mM $Na_3PO_4$, pH 6.8) to 90±5° C. and then cooling them slowly to room temperature over approximately 3 hours.

Example 2

Extraction of Human Serum

For coagulation, a blood sample was immediately incubated in a darkened collecting tube (SST Vacutainer 9.5 mL; BD Vacutainer Systems, Becton Dickinson & Co., Belliver Industrial Estate, Plymouth PL6 7BP, Great Britain) for 2 hours at 20° C. After that, serum was separated as supernatant fluid from agglutinated blood in a centrifuge at 4° C. and 3000×g for 15 minutes (Megafuge 1.0; Heraeus Instruments, Kendro Laboratory Products, 37520 Osterode, Germany), transferred to sterile 1.5 mL reagent vessels (La Fontaine, International GmbH & Co. KG, Daimlerstr. 14, 68753 Waghäusel, Germany), and stored at −20° C.

Example 3

Incubation of dsRNA with Serum

60 µl serum were placed on ice in each of 1.5 mL reagent vessels. Subsequently, 12 µl of a 25 µM dsRNA solution was added to each and mixed thoroughly for 5 seconds using a Vortex Genie2 (Scientific Industries, Inc., Bohemia, N.Y. 11716). The dsRNA concentration was 4.16 µM in a volume of 72 µl. The samples were then incubated in a heat block at 37° C. for 15, 30, 60, 120, and 240 minutes, and then immediately flash frozen in liquid nitrogen. One sample was flash frozen in nitrogen without incubation at 37° C. immediately after dsRNA was added to the serum. The samples were stored at −80° C.

Example 4 dsRNA Isolation

With the exception of a phenol solution, all reagents used for isolation were sterile-filtered and cooled on ice before use.

The samples that were stored at −80° C. were placed on ice; 450 µl of a 0.5 M NaCl solution was then added to each, and mixed thoroughly after thawing for 5 seconds.

DsRNA extraction from the sample solution was done in phase lock gel reagent vessels (Eppendorf AG, 22331 Hamburg, Germany). The phase lock gel reagent vessels were then centrifuged for 2 minutes at 16,100×g and 4° C., and then placed on ice. Subsequently, the samples were transferred to the phase lock gel reagent vessels, to which were added 500 µl of a phenol:chloroform:isoamyl alcohol mixture (Roti-Phenol, Carl Roth GmbH & Co., Schoemperlenstr. 1-5; 76185 Karlsruhe, Germany) and 300 µl chloroform. The samples were then thoroughly mixed for 30 seconds with an IKA Vibrax VXR basic, Type VX2E (IKA Works do Brasil, Ltd, Taquora, RJ 22713-000, Brazil). Subsequent phase separation was done by means of centrifugation at 4° C. and 16,100×g for 15 minutes. The upper aqueous phase was carefully transferred to a new sterile region vessel. After that, 40 µl ice-cooled 3 M sodium acetate solution (pH 5.2) was added to the aqueous phase. The resulting solution was thoroughly mixed for 20 seconds. After the addition of 1 µl Pellet Paint (NF Co-Precipitant, Novagen, 441 Charmony Drive, Madison Wis. 53719) it was mixed for 5 seconds. Thereafter, 1 mL of ice-cooled ethanol was added and shaken for 20 seconds. To precipitate the dsRNA, the solution was cooled for one hour to −80° C.

The precipitated dsRNA was pelleted by means of centrifugation at 12,000×g for 30 minutes at 4° C.; the supernatant fluid was then carefully poured off, and the pellet was washed with 500 µl of ice-cooled 70% ethanol (Mallinckrodt Baker B.V., 7400 AA Deventer, Holland). After shaking for 2 seconds, it was again centrifuged at 12,000×g and 4° C. for 10 minutes, and the supernatant fluid above the pelleted dsRNA was poured off. The remaining solution was collected at the bottom of the vessel by centrifuging for 20 seconds at 16,100×g and 4° C., and then pipetted off. The pelleted dsRNA was dried uncovered for 5 minutes at room temperature.

The dried dsRNA was then dissolved by mixing thoroughly for 2 minutes in 30 µl gel application buffer (95% v/v formamide, 10 mM EDTA, 0.025% w/v xylencyanol, 0.025% w/v bromophenol blue.

Example 5

Analysis by dsRNA Stability

Analysis of the dsRNA was done by means of denaturing polyacrylamide gel electrophoresis in 0.8-mm-thick and 200×280 mm sized gels with 8 M urea and 16% v/v formamide.

| Composition of a gel (50 mL): | |
|---|---|
| 24 g urea | (99.5% p.a.; Carl Roth GmbH & Co., Schoemperlenstr. 1-5, 76185 Karlsruhe, Germany), |
| 18 mL acrylamide | (rotiphoresis gel 29:1 [40%]; Carl Roth GmbH & Co., Schoemperlenstr. 1-5, 76185 Karlsruhe, Germany), |
| 5 mL 10× TBE | (1 M tris [ultra quality; Carl Roth GmbH & Co., Schoemperlenstr, 1-5, 76185 Karlsruhe, Germany] |
| 1 M boric acid | [99.8% p.a., %; Carl Roth GmbH & Co., Schoemperlenstr. 1-5, 76185 Karlsruhe, Germany], |
| 25 mM EDTA | [Sigma-Aldrich Chemie GmbH P.O. 1120, 89552 Steinheim, Germany] in deionized water), |
| 8 mm formamide | (Merck-Schuchardt, 85662 Hohenbrunn, Germany), |
| 50 µl temed | (N,N,N',N'-tetramethyl ethylene diamine) (Sigma-Aldrich Chemie GmbH P.O. 1120, 89552 Steinheim, Germany), and |
| 200 µl APS | ammonium persulfate (10% w/v) (Gibco BRL Life Technologies, Invitrogen GmbH, Karlsruhe Technology Park, Emmy Noether Str. 10, 76131 Karlsruhe, Germany). |

After pouring the gel between two glass plates and polymerizing it for approximately 30 minutes, a first run was done in a gel run apparatus for approximately 30 minutes at 45 mA (power source: Power PAC 3000; Bio Rad Laboratories 2000 Alfred Nobel Drive, Hercules, Calif. 94547). 1×TBE was used as the gel running buffer. In order to equalize the temperature of the gel a 3-mm-thick aluminum plate was affixed to one of the glass plates.

Before application onto the gel, the samples were heated for 5 minutes to 100° C., chilled on ice, and centrifuged for 20 seconds at 13,000×g and 4° C. 10 µl of each sample was applied. In addition, a dsRNA sample that was not incubated with serum (2 µl 25 µM dsRNA in 10 µl gel application buffer) was applied.

Electrophoresis was done for 90 minutes at 45 mA. Finally, the gel was stained for 30 minutes with Stains-all (40 mg Stains-all (1-ethyl-2-[3(3-ethylnaphtho[1,2-d]thiazoline-2-ylidine)-2-methylpropenyl]naphtho-[1,2-d]thiazolium bromide); Sigma-Aldrich Chemie GmbH P.O. 1120, 89552 Steinheim, Germany)+400 mL formamide (Merck-Schuchardt, 85662 Hohenbrunn, Germany)+400 mL $H_2O$), and then de-stained in a water bath for approximately 30-60 minutes. The de-stained gels were digitized using a photodocumentation apparatus (Image Master VDS Pharmacia Biotech; Amersham Biosciences Europe GmbH, Munzinger Str. 9, 79111 Freiburg; by D & R, Israel) and then scanned in color mode (Silver Fast, UMAX Technologies, Inc., 10460 Brockwood Road, Dallas, Tex. 75238; Adobe Photoshop Elements, Adobe Systems, Inc., 345 Park Ave., San Jose, Calif. 95110-2704).

The serum stabilities of each of the following dsRNAs were analyzed.

1. BCL20, whose S1 antisense strand is complementary to a sequence of the sense strand of the human BCL-2 gene (Gene Bank accession number M13994):

```
S2:
5'-GGC GAC UUC GCC GAG AUG UCC-3'  (SEQ ID NO: 7)
S1:
3'-CG CCG CUG AAG CGG CUC UAC AGG-5' (SEQ ID NO: 8)
```

2. B133, whose S1 antisense strand is complementary to the sense strand of the human bcl-2 gene (Gene Bank accession no. M13994):

```
S2: 5'-ACC GGG CAU CUU CUC CUC CCA-  (SEQ ID NO: 9)
    3'
S1: 3'-CG UGG CCC GUA GAA GAG GAG   (SEQ ID NO: 10)
    GGU-5'
```

3. P3, whose S1 antisense strand is complementary to the sense strand of the human PLK1 gene (Gene Bank accession no. X75932):

```
S2: 5'-GAU CAC CCU CCU UAA AUA UUU-  (SEQ ID NO: 11)
    3'
S1: 3'-CG CUA GUG GGA GGA AUU UAU   (SEQ ID NO: 12)
    AAA-5'
```

Figure 2:
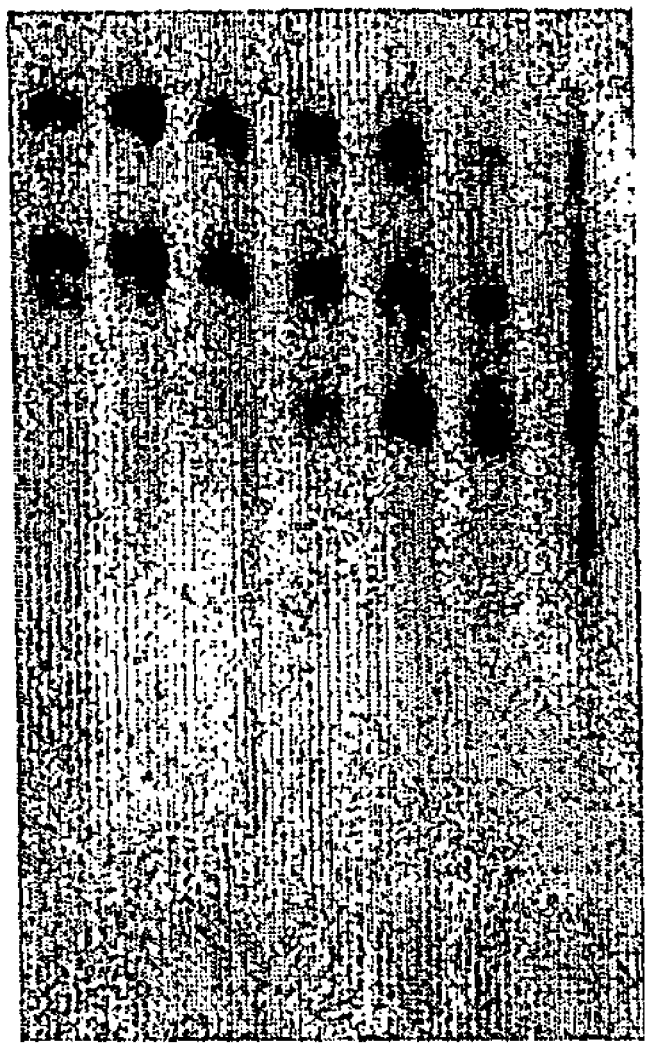
FIG. 2 is a gel electrophoretic separation of another dsRNA that is the subject of this invention without incubation, and after 0, 15, 30, 60, 120, and 240 minutes incubation in serum.
Figure 3:
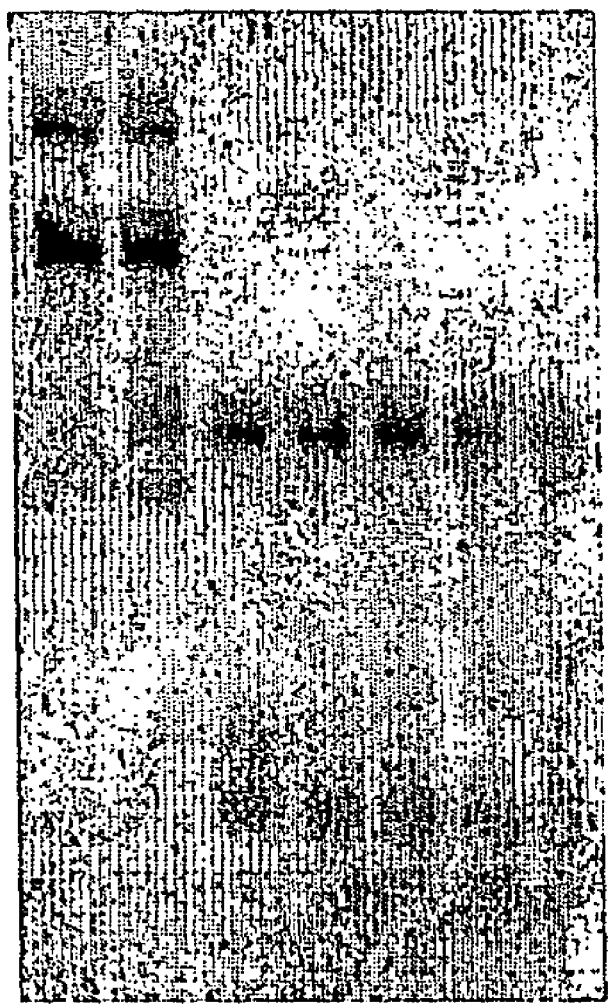
FIG. 3 is a gel electrophoretic separation of a conventional dsRNA without incubation, and after 0, 15, 30, 60, 120, and 240 minutes incubation in serum.

FIGS. 1 to 3 each show from left to right a gel electrophoretic separation of a dsRNA without and after 0, 15, 30, 60, 120, and 240 minutes of incubation in serum. FIG. 1 shows the gel electrophoretic separation of BCL20 dsRNA, which shows negligible degradations during incubation. FIG. 2 the gel electrophoretic separation of B133 dsRNA, in which neither of the terminal pairs are G-C parids. B133 is degraded at a higher rate than BCL20 dsRNA. FIG. 3 the gel electrophoretic separations of P3 dsRNA. Conventional dsRNA, such as P3 dsRNA shown in FIG. 3, is degraded almost immediately in serum. P3 dsRNA exhibits complementary G-C nucleotide pairs only at one end of the double-stranded structure.

Example 6

Increased Melting Temperature of Modified Plk1 Specific siRNAs

The melting temperatures of two Plk1 specific siRNAs (i.e., P2 and P4) differing only in their 3' nucleotide overhangs were determined. The following two siRNAs were synthesized by standard methods:

```
1. P2: 5'-UCAGACACCUCACUUAUUAUU-3'  (SEQ ID NO: 44)
       3'-UUAGUCUGUGGAGUGAAUAAUA   (SEQ ID NO: 45)
       A-5'

2. P4: 5'-GCAGACACCUCACUUAUUAUU-3'  (SEQ ID NO: 46)
       3'-CGCGUCUGUGGAGUGAAUAAUA   (SEQ ID NO: 47)
       A-5'
```

To anneal the duplex structures, 20 µM solutions in PBS/100 mM NaCl were heated to 95° C. and then cooled at a rate of 1° C./min. The solutions were diluted 1:4 with the same buffer. Melting temperatures (Tm) for the duplexes were measured in a BeckmannCoulter UV/VIS Spectrometer at 260 nm. The temperature was raised from 30° C. to 95° C. at 0.5° C. and the absorbance of the solution was measured after each increase of 1° C. Thereafter, the same procedure was followed in cooling. The Tm was calculated using the 2-point-average algorithm included in the software package provided with the UV spectrometer.

The Tm was determined as 67° C. for P2 and 69.6° C. for P4. Since the only difference between the duplex structures lies in the 3'-overhang, it is reasonable to conclude that the overhang is causing this difference.

The increased Tm may be understood by looking at the free energy contributions of the overhang nucleotides. The 3'-CG-overhang contributes the largest decrease in free energy for the duplex (see Freier, S. M., et al., PNAS 1986, 83:9373-9377). This effectively reduces the amount of fraying (i.e., opening and closing) of the strand ends. Since the opening of the duplex is believed to be necessary for exonucleases to gain access to degrade the strand ends, this increased thermodynamic stability of the duplex terminus translates into a higher resistance to exonucleolytic degradation.

Incorporation by Reference

All of the U.S. patents and U.S. patent application publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A double-stranded ribonucleic acid (dsRNA), consisting of first and second single RNA strands, wherein the first single RNA strand is an antisense RNA strand, the second single RNA strand is a sense RNA strand, wherein the antisense RNA strand is complementary to a target gene or a portion thereof, the dsRNA having increased effectiveness in inhibiting the expression of a target gene by means of RNA interference, wherein the dsRNA comprises first and second double-stranded ends and at least one single-stranded overhang which is 2 to 4 nucleotides in length, wherein the unpaired nucleotide of the single-stranded overhang that is directly adjacent to the terminal nucleotide base pair comprises a purine base, wherein a single-stranded overhang is located at the 3'-end of the antisense strand, wherein the overhang comprises the sequence 5'-GC-3'; and wherein the terminal base pair of the first double-stranded end comprises a guanine-cytosine (G-C) base pair or the four consecutive terminal base pairs of the first double-stranded end comprises at least two G-C base pairs; wherein the terminal base pair of the second double-stranded end comprises a guanine-cytosine (G-C) base pair or the four consecutive terminal base pairs of the second double-stranded end comprises at least two G-C base pairs; wherein the region of the antisense strand that is complementary to the targer gene is 19-28 nucleotides in length excluding the following dsRNAs:

```
5'- CAGGACCUCGCCGCUGCAGACC-3'      (SEQ ID NO: 1)

3'-CGGUCCUGGAGCGGCGACGUCUGG-5',    (SEQ ID NO: 2)

5'- UGCAGCUUCGAAGCCUCACAGA-3'      (SEQ ID NO: 27)

3'-CGACGUCGAAGCUUCGGAGUGU-5',      (SEQ ID NO: 28)
and

5'- UGGGGAGAGAGUUCUGAGGAUU-3'      (SEQ ID NO: 29)

3'-CGACCCCUCUCUCAAGACUCCU-5'       (SEQ ID NO: 30).
```

2. The dsRNA of claim 1, wherein each nucleotide overhang independently consists of 2 unpaired nucleotides.

3. The dsRNA of claim 1, wherein at least half of the unpaired nucleotides comprise a purine base.

4. The dsRNA of claim 1, wherein the unpaired nucleotide adjacent to the terminal nucleotide base pair comprises a guanine (G).

5. The dsRNA of claim 1, wherein the unpaired nucleotide adjacent to the terminal nucleotide base pair comprises an adenine (A) base.

6. The dsRNA of claim 1, wherein said nucleotide overhang comprising the sequence 5'-GC-3' consists of the sequence 5'-GC-3'.

7. The dsRNA of claim 1, wherein the region of the antisense strand that is complementary to the target gene is 19 to 24 nucleotides in length.

8. The dsRNA of claim 1, wherein the antisense strand is 20 to 28 nucleotides in length.

9. The dsRNA of claim 1, wherein the antisense strand is 21 nucleotides in length.

10. The dsRNA of claim 1, wherein at least one of the RNA strands comprises at least one chemically modified nucleotide.

11. The dsRNA of claim 10, wherein the chemically modified nucleotide comprises a non-natural base.

12. The dsRNA of claim 10, wherein the chemically modified nucleotide comprises a 2' modification.

13. The dsRNA of claim 12, wherein the 2'modification is selected from the group consisting of a 2'-amino modification, a 2'-alkyl modification, a 2'-O -methyl modification, a 2'-O-ethyl modification, a 2'-O-propyl modification, a 2'-O-allyl modification, a 2'-O-aminoalkyl modification, and a 2'-deoxy-2'-fluoro modification.

14. A method for the targeted selection of a double-stranded ribonucleic acid (dsRNA), consisting of first and second single RNA strands, wherein the first single RNA strand is an antisense RNA strand, the second single RNA strand is a sense RNA strand, wherein the antisense RNA strand is complementary to a target gene or a portion thereof, the dsRNA having increased effectiveness in inhibiting the expression of a target gene by means of RNA interference, comprising the steps of:
   (a) selecting a dsRNA comprising first and second double-stranded ends and at least one single-stranded overhang which is 2 to 4 nucleotides in length;
   (b) selecting a dsRNA comprising first and second double-stranded ends, wherein the unpaired nucleotide of the single-stranded overhang that is directly adjacent to the terminal nucleotide base pair comprises a purine base, wherein a single-stranded overhang is located at the 3'-end of the antisense strand, and wherein the overhang comprises the sequence 5'-GC-3'; and
   (c) selecting a dsRNA comprising first and second double-stranded ends, wherein terminal base pair of the first double-stranded end comprises a guanine-cytosine (G-C) base pair or the four consecutive terminal base pairs of the first double-stranded end comprises at least two G-C base pairs; wherein the terminal base pair of the second double-stranded end comprises a guanine-cytosine (G-C) base pair or the four consecutive terminal base pairs of the second double-stranded end comprises at least two G-C base pairs; wherein the region of the antisense strand that is complementary to the target gene is 19-28 nucleotides in length;
excluding the following dsRNAs:

```
5'- CAGGACCUCGCCGCUGCAGACC-3'      (SEQ ID NO: 1)

3'-CGGUCCUGGAGCGGCGACGUCUGG-5',    (SEQ ID NO: 2)

5'- UGCAGCUUCGAAGCCUCACAGA-3'      (SEQ ID NO: 27)

3'-CGACGUCGAAGCUUCGGAGUGU-5',      (SEQ ID NO: 28)
and

5'- UGGGGAGAGAGUUCUGAGGAUU-3'      (SEQ ID NO: 29)

3'-CGACCCCUCUCUCAAGACUCCU-5'       (SEQ ID NO: 30).
```

15. The method of claim 14, wherein each nucleotide overhang independently consists of 2 unpaired nucleotides.

16. The methods of claim 14, wherein at least half of the unpaired nucleotides comprise a purine base.

17. The method of claim 14, wherein the unpaired nucleotide adjacent to the terminal nucleotide base pair comprises a guanine (G) base.

18. The method of claim 14, wherein the unpaired nucleotide adjacent to the terminal nucleotide base pair comprises an adenine (A) base.

19. The method of claim 14, wherein said nucleotide overhang comprising the sequence 5'-GC-3' consists of the sequence 5'-GC-3'.

20. The method of claim 14, wherein the region of the antisense strand that is complementary to the target gene is 19 to 24 nucleotides in length.

21. The method of claim 14, wherein the antisense strand is 20 to 28 nucleotides in length.

22. The method of claim 14, wherein the antisense strand is 21 nucleotides in length.

23. The method of claim 14, wherein at least one of the RNA strands comprises at least one chemically modified nucleotide.

24. The method of claim 23, wherein the chemically modified nucleotide comprises a non-natural base.

25. The methods of claim 23, wherein the chemically modified nucleotide comprises a 2' modification.

26. The method of claim 25, wherein the 2' modification is selected from the group consisting of a 2'-amino modification, a 2'-alkyl modification, and a 2'-O-methyl modification, a 2'-O-ethyl modification, a 2'-O-propyl modification, a 2'-O-allyl modification, a 2'-O-aminoalkyl modification, and a 2'-deoxy-2'-fluoro modification.

27. A pharmaceutical composition for inhibiting the expression of a target gene by means of RNA interference, comprising a dsRNA of claim 1, or a salt, prodrug or hydrate thereof; and a pharmaceutically acceptable carrier.

28. A method for inhibiting the expression of a target gene in a cell, comprising:
   (a) introducing into the cell a dsRNA of claim 1, or a salt, prodrug or hydrate thereof; and
   (b) maintaining the cell for a time sufficient to obtain degradation of a mRNA transcript of the target gene.

29. The method of claim 28, wherein the cell is a mammalian cell.

30. The method of claim 29, wherein the cell is a human cell.

31. The method of claim 28, wherein the target gene is selected from the group consisting of 11-hyroxysteroid dehydrogenase-1, acetyl-CoA-carboxylase-2, acyl CoA:

DAG acyltransferase1, Adenosine A2 receptor, akt, AML-ETO, amyloid beta precursor protein (APP), ApoAl, ApoB, ApoM, APS (adaptor protein with pleckstrin homology and src homology 2 domains, a-synuclein, Aurora A, Aurora B, beta-1 integrin subunit, beta-amyloid converting enzyme (BACE), Bax, beta-catenin, Bcl2, Bcl-XL, Bcr- abl, caspase 8, caspase-3, C CR2, CD40, CD40L, cdk2, chk1, chk2, clottingfactorVII, collagen, CD132, CTLA4, cyclin E, Dhcr24, Dipeptidylpeptidase-IV, E-Cadherin, Eg5/KSP, EGF, EGFR1, EWS-Flil, FAS-fatty acid synthase, FoxA-3, FoxO-1, Fructose-1,6-bisphosphate, Glucose-6-phophate, GM3 synthase, HDAC (histone deacetylase 1-6,9), Her-2/erb2, HIF1, HMG CoA reductase, hormone sensitive lipase, huntingtin, IKK1, IKK2, LDLR, MDR1, Microsomal Triglyceride Transfer Protein, MMP1, MMP2, MMP9, MyD88, sodium voltage gated type X alpha polypeptide (NaV1.8), NFkB, p38 map kinase mitogen activated protein kinase, p85a regulatory subunit of PI3-kinase, PEPCK, plkl, PTEN, PTP-1B, PU.1, raf, ras, Resistin, SCAP, SERBP-2, SHIP-2, SMAD7, SREBP1C, STAT1, stearoyl-CoA desaturase-1, TERT, TGF-beta-1, TGF-beta-1R1, Topoisomerase I, Topoisomerase II, VEGF, VEGFR1, VEGFR2, VLA1, VLA4, and vanilloid receptor (VR1).

* * * * *

SEQUENCE LISTING

```
<160> NUMBER OF SEQ ID NOS: 47

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
caggaccucg ccgcugcaga cc                                                   22

<210> SEQ ID NO 2
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggucugcagc ggcgaggucc uggc                                                 24

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gccuuugugg aacuguacgg cc                                                   22

<210> SEQ ID NO 4
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggccguacag uuccacaaag gcau                                                 24

<210> SEQ ID NO 5
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 5
cuucuccgcc ucacaccgcu gcaa                                          24

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gcagcggugu gaggcggaga ag                                            22

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggcgacuucg ccgagauguc c                                             21

<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggacaucucg gcgaagucgc cgc                                           23

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
accgggcauc uucuccuccc a                                             21

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ugggaggaga agaugcccgg ugc                                           23

<210> SEQ ID NO 11
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 11
gaucacccuc cuuaaauauu u                                              21

<210> SEQ ID NO 12
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aaauauuuaa ggagggugau cgc                                            23

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
acggcuagcu gugaaagguc c                                              21

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ggaccuuuca cagcuagccg uga                                            23

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
caaggagcag ggacaaguua c                                              21

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
guaacuuguc ccugcuccuu gaa                                            23

<210> SEQ ID NO 17
<211> LENGTH: 23
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 17
cacguacgcg gaauacuucg aaa                                               23

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ucgaaguauu ccgcguacgu g                                                 21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ccgcuugacu gcagagagug c                                                 21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
acucucugca gucaagcggc u                                                 21

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
caucuucuuc aaggacgacg gc                                                22

<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cgucguccuu gaagaagaug gu                                                22

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 23
gguggcgcug gaugguaagc cgc                                              23

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ggcuuaccau ccagcgccac cau                                              23

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uccccaggag gccugcggga gc                                               22

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ucccgcaggc cuccugggga gg                                               22

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ugcagcuucg aagccucaca ga                                               22

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ugugaggcuu cgaagcugca gc                                               22

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 29
uggggagaga guucugagga uu                                              22

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uccucagaac ucucucccca gc                                              22

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
accuccgcaa caacuacgcg c                                               21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gcguaguugu ugcggaggua g                                               21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
guagaccuug cuacugccug c                                               21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
aggcaguagc aagucuacc a                                                21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 35
caugacggaa cuagagacag c                                              21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ugucucuagu uccgucaugg u                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cucuacgcuu guacgaggag c                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uccucguaca agcguagaga c                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cagacuucgg aguaccugcg c                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gcagguacuc cgaagucugu u                                              21

<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
```

-continued caucuucuuc aaggacgacg gc                                    22

<210> SEQ ID NO 42
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cgucguccuu gaagaagaug gu                                    22

<210> SEQ ID NO 43
<211> LENGTH: 23
<212> TYPE: DNA
<213> ORGANISM: Mus sp.

<400> SEQUENCE: 43
aagctggccc tggacatgga gat                                   23

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ucagacaccu cacuuauuau u                                     21

<210> SEQ ID NO 45
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aauaauaagu gaggugucug auu                                   23

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gcagacaccu cacuuauuau u                                     21

<210> SEQ ID NO 47
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aauaauaagu gaggugucug cgc                                   23